(12) United States Patent
Ehata

(10) Patent No.: US 7,075,314 B2
(45) Date of Patent: Jul. 11, 2006

(54) METHOD AND APPARATUS FOR MEASURING COMPLEX DIELECTRIC CONSTANT OF DIELECTRIC

(75) Inventor: Katsufumi Ehata, Tokyo (JP)

(73) Assignee: TDK Corporation, Tokyo (JP)

(*) Notice: Subject to any disclaimer, the term of this patent is extended or adjusted under 35 U.S.C. 154(b) by 17 days.

(21) Appl. No.: 10/812,887

(22) Filed: Mar. 31, 2004

(65) Prior Publication Data
US 2004/0246079 A1 Dec. 9, 2004

(30) Foreign Application Priority Data

| Mar. 31, 2003 | (JP) | ............................. 2003-096424 |
| Jul. 31, 2003 | (JP) | ............................. 2003-283591 |
| Jul. 31, 2003 | (JP) | ............................. 2003-283592 |
| Jul. 31, 2003 | (JP) | ............................. 2003-283593 |
| Mar. 3, 2004 | (JP) | ............................. 2004-059742 |

(51) Int. Cl.
*G01R 27/04* (2006.01)
*H01P 7/10* (2006.01)

(52) U.S. Cl. .................................. 324/639; 333/219.1

(58) Field of Classification Search ............... 324/637, 324/638, 639; 333/219.1
See application file for complete search history.

(56) References Cited

U.S. PATENT DOCUMENTS

| 2,867,781 | A | * | 1/1959 | Tomiyasu | ................... | 333/202 |
| 4,866,371 | A | * | 9/1989 | De | .............................. | 324/639 |
| 5,334,941 | A | * | 8/1994 | King | .......................... | 324/637 |
| 5,594,351 | A | * | 1/1997 | Hearn | ........................ | 324/637 |
| 5,625,293 | A | * | 4/1997 | Marrelli et al. | ............. | 324/638 |
| 6,617,861 | B1 | * | 9/2003 | Joshi | .......................... | 324/637 |
| 6,656,864 | B1 | * | 12/2003 | Okawa | ........................ | 501/136 |
| 6,879,166 | B1 | * | 4/2005 | May et al. | .................. | 324/636 |

OTHER PUBLICATIONS

Xi et al. "Field Analysis of New Coaxial Dielectrometer" Oct. 1992, IEEE Transactions on Microwave Theory and Techniques; pp. 1927-1934.*

Hua et al. "A Mixture Approach with Perturbation Technique for Microwave Characterization of Conducting Polymers" 1995, IEEE; pp. 501-504.*

(Continued)

*Primary Examiner*—Anjan Deb
*Assistant Examiner*—Jeff Natalini
(74) *Attorney, Agent, or Firm*—Oblon, Spivak, McClelland, Maier & Neustadt, P.C.

(57) ABSTRACT

An electromagnetic wave is input to a resonator 14 filled with a dielectric and a gas, and a resonance frequency, an insertion loss and a half-power width in the resonance mode of the electromagnetic wave output from the resonator 14 are measured by a network analyzer 16 in response to the input of the electromagnetic wave and the complex dielectric constant of the dielectric is calculated from the resonance frequency, the insertion loss and the half-power width which are thus measured.

41 Claims, 17 Drawing Sheets

OTHER PUBLICATIONS

B. A. Galwas, et al., IEEE Transactions on Instrumentation and Measurement, vol. 46, No. 2, XP-000725675, pp. 511-514, "Dielectric Measurements Using a Coaxial Resonator Opened to a Waveguide Below Cut-Off", Apr. 1, 1997.

S. O. Nelson, et al., IEEE Transactions on Instrumentation and Measurement, vol. 47, No. 5, XP-000862430, pp. 1201-1204, "Sensing Pulverized Material Mixture Proportions by Resonant Cavity Measurements", Oct. 1998.

Y. Iijima, pp. 20-23, "Electronic Monthly", 1998.

Jis R 1627, Japanese Standards Association, pp. 1-18, "Testing Method for Dielectric Properties of Fine Ceramics at Microwave Frequency", Jul. 1996.

Jis R 1641, Japanese Standards Association, pp. 1-29, "Testing Method for Dielectric Properties of Fine Ceramic Plates at Microwave Frequency", Jan. 2002.

Y. Iijima, pp. 20-23, "Electronic Monthly", 1998.

Jis R 1627, Japanese Standards Association, pp. 1-18, "Testing Method for Dielectric Properties of Fine Ceramics at Microwave Frequency", Jul. 1996.

Jis R 1641, Japanese Standards Association, pp. 1-29, "Testing Method for Dielectric Properties of Fine Ceramic Plates at Microwave Frequency", Jan. 2002.

* cited by examiner

FIG. 26

| TYPE | DIELECTRIC CONSTANT OF SINTERED PRODUCT | MEASURED VALUE |
| --- | --- | --- |
| $Al_2O_3$ | 11 | 14.1 |
| $Ba(MgTa)O_3$ | 24 | 33.9 |
| $TiO_2$ | 104 | 185.8 |

FIG. 27

| TYPE | DIELECTRIC CONSTANT OF SINTERED PRODUCT | MEASURED VALUE |
| --- | --- | --- |
| $Al_2O_3$ | 11 | 15.7 |
| $Ba(MgTa)O_3$ | 24 | 19.4 |
| $TiO_2$ | 104 | 28.2 |

FIG. 28

| TYPE | DIELECTRIC CONSTANT OF SINTERED PRODUCT | MEASURED VALUE |
| --- | --- | --- |
| $Al_2O_3$ | 11 | 8.75 |
| $Ba(MgTa)O_3$ | 24 | 42.7 |
| $TiO_2$ | 104 | 152.3 |

| TYPE | DIELECTRIC CONSTANT OF SINTERED PRODUCT | DIELECTRIC CONSTANT OF MIXTURE WITH 0.38 OF VOLUME RATIO OF POWDER |
|---|---|---|
| $Al_2O_3$ | 11 | 2.7 |
| $Ba(MgTa)O_3$ | 24 | 3.8 |
| $TiO_2$ | 104 | 7.3 |

METHOD AND APPARATUS FOR MEASURING COMPLEX DIELECTRIC CONSTANT OF DIELECTRIC

BACKGROUND OF THE INVENTION

The present invention relates to a method and apparatus for measuring the complex dielectric constant of a dielectric, and more particularly to a method and apparatus for measuring the complex dielectric constant of a dielectric which can measure the complex dielectric constant of a dielectric with high precision.

With an enhancement in the performance of various radio devices, there has been required a ceramics dielectric for a high frequency having a high performance in a high frequency band of several GHz or more. In general, the ceramics dielectric has been used as a circuit component in the form of a burned product obtained by burning a powder-like dielectric. Moreover, a composite dielectric obtained by mixing the powder-like dielectric and a resin at various ratios has also been used as the circuit component.

In order to develop the ceramics dielectric for a high frequency, accordingly, it is indispensable that the complex dielectric constant of the dielectric is measured as the dielectric characteristic of the dielectric corresponding to the state of a powder and a burned product.

A dielectric constant in the complex dielectric constant of the powder-like dielectric has been calculated as follows. For example, a container having a pair of electrodes provided to be opposed to each other at a constant interval is filled with the powder-like dielectric of which dielectric constant is to be measured, a voltage is applied to a portion between the electrodes, and the dielectric constant of a mixture obtained by mixing the powder-like dielectric and air is measured. Thus, the dielectric constant is calculated from the dielectric constant of the mixture which is thus measured (see Patent Document 1).

On the other hand, the complex dielectric constant of a powder-like dielectric molding formed by burning is generally measured by using a perturbation method, a cavity resonator method and a dielectric resonator method (see Non-Patent Documents 1, 2 and 3). In the perturbation method, the cavity resonator method and the dielectric resonator method, it is required that a dielectric molding to be a measuring object takes a predetermined shape defined by each of the measuring methods. For example, it is required that the dielectric to be the measuring object is formed like a slender bar in the perturbation method, a sheet in the cavity resonator method and a cylinder in the dielectric resonator method.

[Patent Document 1] JP-A-6-138076

[Non-Patent Document 1] Yasushi Iijima, "Electronic Monthly", Shinko Shoji Co., Ltd., July 1998

[Non-Patent Document 2] JIS R 1627: 1996 "Method of Testing Dielectric Characteristic of Fine Ceramics for Microwave", Japanese Standards Association, July 1996

[Non-Patent Document 3] JIS R 1641: 2002 "Method of Testing Microwave Dielectric Characteristic of Fine Ceramics Board", Japanese Standards Association, January, 2002

In a conventional method of measuring the dielectric constant of a powder-like dielectric, however, in the case in which the dielectric constant of the powder-like dielectric is to be measured in a high frequency band of several GHz or more, the presence of a floating capacity and a floating reactance cannot be disregarded. As a result, there is a problem in that a whole measuring apparatus resonates and the dielectric constant of the powder-like dielectric cannot be thus measured with high precision. Moreover, there has not conventionally been known a practical method of measuring a dielectric loss tangent in the complex dielectric constant of the powder-like dielectric as desired.

On the other hand, although the dielectric molding can easily be formed cylindrically depending on the type of the dielectric, it is hard to form the dielectric molding to take the shape of a slender bar or a plate. Consequently, there is a problem in that the complex dielectric constant of the dielectric cannot be measured by using the perturbation method or the cavity resonator method. On the other hand, in the dielectric resonator method capable of measuring a cylindrical dielectric molding, there is a problem in that a dielectric constant and a dielectric loss tangent cannot be measured in a dielectric having a low dielectric constant in a complex dielectric constant, for example, a resin.

SUMMARY OF THE INVENTION

In consideration of the circumstances, it is an object of the invention to provide a method and apparatus for measuring the complex dielectric constant of a powder-like dielectric, a powder-like dielectric in which the complex dielectric constant of a dielectric molding can be measured, or a dielectric molding with high precision also in a high frequency band of several GHz or more.

(1) A method of measuring a complex dielectric constant of a dielectric, comprising the steps of:
   filling a mode generator with a dielectric;
   inputting an electromagnetic wave to the mode generator;
   measuring an electromagnetic wave output from the mode generator; and
   calculating a complex dielectric constant based on the electromagnetic wave thus measured.

(2) The method of measuring a complex dielectric constant of a dielectric according to (1), wherein the dielectric is a powder-like dielectric,
   the mode generator is filled with a gas together with the dielectric,
   an S parameter in a resonance mode of the electromagnetic wave is measured at the measuring step, and
   the calculating step includes a step of calculating a complex dielectric constant of a mixture obtained by mixing the dielectric and the gas in the mode generator based on the S parameter, and
   a step of calculating the complex dielectric constant of the dielectric from the complex dielectric constant of the mixture which is thus calculated and a volume ratio of the dielectric in the mixture.

(3) The method of measuring a complex dielectric constant of a dielectric according to (2), wherein the calculation of the complex dielectric constant of the mixture is a calculation of a dielectric constant of the mixture, and the calculation of the complex dielectric constant of the dielectric is a calculation of a dielectric constant of the dielectric.

(4) The method of measuring a complex dielectric constant of a dielectric according to (3), wherein the dielectric constant of the dielectric is calculated by using one of a logarithmic alligation, an equation of "Lichteneker Rother" and an equation of Wiener.

(5) The method of measuring a complex dielectric constant of a dielectric according to any of (2) to (4), wherein the calculation of the complex dielectric constant of the mixture is a calculation of a dielectric loss tangent of the mixture, and the calculation of the complex dielectric constant of the dielectric is a calculation of a dielectric loss tangent of the dielectric.

(6) The method of measuring a complex dielectric constant of a dielectric according to (5), wherein the calculation of the dielectric loss tangent of the dielectric is carried out by using an equation of the alligation.

(7) The method of measuring a complex dielectric constant of a dielectric according to (1), wherein the dielectric is a dielectric molding having the same section as a section of a closed space of the mode generator, the mode generator is filled with a gas together with the dielectric, a resonance frequency, an insertion loss and a half-power width in a resonance mode of the electromagnetic wave are measured at the measuring step, and a complex dielectric constant of the dielectric molding is calculated, at the calculating step, from the resonance frequency, the insertion loss and the half-power width which are thus measured.

(8) The method of measuring a complex dielectric constant of a dielectric according to (7), wherein the calculation of the complex dielectric constant of the dielectric molding is a calculation of a dielectric constant of the dielectric molding.

(9) The method of measuring a complex dielectric constant of a dielectric according to (7), wherein the calculation of the complex dielectric constant of the dielectric molding is a calculation of a dielectric loss tangent of the dielectric molding.

(10) The method of measuring a complex dielectric constant of a dielectric according to any of (7) to (9), wherein the dielectric molding is columnar.

(11) The method of measuring a complex dielectric constant of a dielectric according to any of (2) to (10), wherein the mode generator is a cylindrical resonator.

(12) The method of measuring a complex dielectric constant of a dielectric according to any of (2) to (10), wherein the mode generator is a cavity resonator.

(13) The method of measuring a complex dielectric constant of a dielectric according to any of (2) to (12), wherein the resonance mode of the electromagnetic wave is a $TE_{011}$ mode.

(14) The method of measuring a complex dielectric constant of a dielectric according to any of (1) to (13), further comprising a step of drying the dielectric in the mode generator.

(15) The method of measuring a complex dielectric constant of a dielectric according to (14), further comprising a step of evacuating the mode generator, thereby drying the dielectric.

(16) The method of measuring a complex dielectric constant of a dielectric according to (1), wherein the mode generator is a waveguide, the waveguide is filled with a gas or a liquid together with the dielectric, a dielectric constant of a mixture obtained by mixing a powder and the gas or liquid is calculated based on the measured electromagnetic wave at the calculating step, and a dielectric constant of the powder is calculated from the dielectric constant of the mixture and a volume ratio of the powder in the mixture at the calculating step.

(17) The method of measuring a complex dielectric constant of a dielectric according to (16), wherein a dielectric constant of the dielectric is calculated by using one of a logarithmic alligation, an equation of "Lichteneker Rother" and an equation of Wiener.

(18) The method of measuring a complex dielectric constant of a dielectric according to (16) or (17), wherein the waveguide is a coaxial-type waveguide.

(19) The method of measuring a complex dielectric constant of a dielectric according to (16) or (17), wherein the waveguide is a reqtangular waveguide.

(20) The method of measuring a complex dielectric constant of a dielectric according to (16) or (17), wherein the waveguide is a circular waveguide.

(21) The method of measuring a complex dielectric constant of a dielectric according to any of (16) to (20), wherein the waveguide includes a seal portion for holding the gas or the liquid.

(22) The method of measuring a complex dielectric constant of a dielectric according to any of (16) to (21), wherein a volume ratio of the powder in the mixture is set to be 0.32 to 0.42 and a frequency of the electromagnetic wave is 0.1 GHz or more.

(23) The method of measuring a complex dielectric constant of a dielectric according to (17), further comprising the steps of:

measuring respective dielectric constants of a plurality of mixtures in which types of powders are different from each other and volume ratios are equal to each other, and comparing the dielectric constants of the mixtures, thereby comparing and measuring dielectric constants of a plurality of dielectrics.

(24) An apparatus for measuring a complex dielectric constant of a dielectric, comprising:

a mode generator having a dielectric provided therein;

an electromagnetic wave generating analyzer for inputting an electromagnetic wave to the mode generator provided with the dielectric and measuring the electromagnetic wave output from the mode generator in response to the input of the electromagnetic wave; and a calculating device for calculating the complex dielectric constant of the dielectric based on the electromagnetic wave thus measured.

(25) The apparatus for measuring a complex dielectric constant of a dielectric according to (24), wherein the mode generator is a resonator for filling the dielectric and a gas therein, the electromagnetic wave generating analyzer measures a resonance frequency, an insertion loss and a half-power width in a resonance mode of the electromagnetic wave, and the calculating device calculates the complex dielectric constant of the dielectric based on the resonance frequency, the insertion loss and the half-power width.

(26) The apparatus for measuring a complex dielectric constant of a dielectric according to (25), wherein the resonator includes:

a first piston provided with a through hole;

a second piston provided opposite to the first piston;

a cylinder for covering the first piston and the second piston, thereby forming a closed space; and a coaxial cable for inputting and outputting the electromagnetic wave inserted in the through hole.

(27) The apparatus for measuring a complex dielectric constant of a dielectric according to (26), wherein an annular groove is formed on a tip portion of the first piston and a tip portion of the second piston.

(28) The apparatus for measuring a complex dielectric constant of a dielectric according to (26), wherein an annular conductor or dielectric plate is attached to a tip portion of the first piston and a tip portion of the second piston.

(29) The apparatus for measuring a complex dielectric constant of a dielectric according to any of (25) to (28), wherein when the dielectric is a powder, the calculating device calculates a complex dielectric constant of a mixture obtained by mixing the dielectric and the gas in the resonator from the resonance frequency, the insertion loss and the half-power width which are measured, and calculates the complex dielectric constant of the dielectric from the complex dielectric constant of the mixture which is thus calculated and a volume ratio of the dielectric in the mixture.

(30) The apparatus for measuring a complex dielectric constant of a dielectric according to (29), wherein the calculation of the complex dielectric constant of the mixture is a calculation of a dielectric constant of the mixture, and the calculation of the complex dielectric constant of the dielectric is a calculation of a dielectric constant of the dielectric.

(31) The apparatus for measuring a complex dielectric constant of a dielectric according to (30), wherein the dielectric constant of the dielectric is calculated by using one of a logarithmic alligation, an equation of "Lichteneker Rother" and an equation of Wiener.

(32) The apparatus for measuring a complex dielectric constant of a dielectric according to (29), wherein the calculation of the complex dielectric constant of the mixture is a calculation of a dielectric loss tangent of the mixture, and the calculation of the complex dielectric constant of the dielectric is a calculation of a dielectric loss tangent of the dielectric.

(33) The apparatus for measuring a complex dielectric constant of a dielectric according to (32), wherein the dielectric loss tangent of the dielectric is calculated by using an equation of the alligation.

(34) The apparatus for measuring a complex dielectric constant of a dielectric according to any of (25) to (28), wherein when the columnar dielectric is a molding, the calculating device calculates a complex dielectric constant of the dielectric molding from the resonance frequency, the insertion loss and the half-power width which are measured.

(35) The apparatus for measuring a complex dielectric constant of a dielectric according to (34), wherein the calculation of the complex dielectric constant of the dielectric molding is a calculation of a dielectric constant of the dielectric molding.

(36) The apparatus for measuring a complex dielectric constant of a dielectric according to (34), wherein the calculation of the complex dielectric constant of the dielectric molding is a calculation of a dielectric loss tangent of the dielectric molding.

(37) The apparatus for measuring a complex dielectric constant of a dielectric according to any of (25) to (36), wherein the resonance mode of the electromagnetic wave is a $TE_{011}$ mode.

(38) The apparatus for measuring a complex dielectric constant of a dielectric according to any of (25) to (37), further comprising a vacuum device for evacuating a closed space in the resonator to dry the dielectric in the resonator.

(39) The apparatus for measuring a complex dielectric constant of a dielectric according to any of (34) to (36), wherein the resonator is filled with a columnar dielectric molding having the same section as a section of the closed space and a gas.

(40) The apparatus for measuring a complex dielectric constant of a dielectric according to any of (25) to (39), wherein the dielectric and the gas are filled in a closed space having an almost circular section which is formed in the resonator.

(41) The apparatus for measuring a complex dielectric constant of a dielectric according to (24), wherein the mode generator is a waveguide filled with a mixture obtained by mixing a powder of which complex dielectric constant is to be measured and a gas or a liquid.

According to the invention, it is possible to provide a method and apparatus for measuring the complex dielectric constant of a dielectric which can measure the complex dielectric constant of a powder-like dielectric with high precision also in a high frequency band of several GHz or more.

BRIEF DESCRIPTION OF THE DRAWINGS

FIG. 26 is a table showing the dielectric constant of each powder obtained by applying the logarithmic alligation to the measured value, FIG. 27 is a table showing the dielectric constant of each powder obtained by applying the equation of "Lichteneker Rother" to the measured value, FIG. 28 is a table showing the dielectric constant of each powder obtained by applying the equation of Wiener to the measured value.

DETAILED DESCRIPTION OF THE PREFERRED EMBODIMENTS

Preferred embodiments of the invention will be described below in detail with reference to the accompanying drawings.

First of all, the basic principle of a method of measuring the complex dielectric constant of a dielectric according to the invention will be roughly described before the detailed explanation of the embodiments. In the following description, the "complex dielectric constant of a powder-like dielectric" implies the dielectric constant of a dielectric and the dielectric loss tangent of the dielectric.

Figure 1:
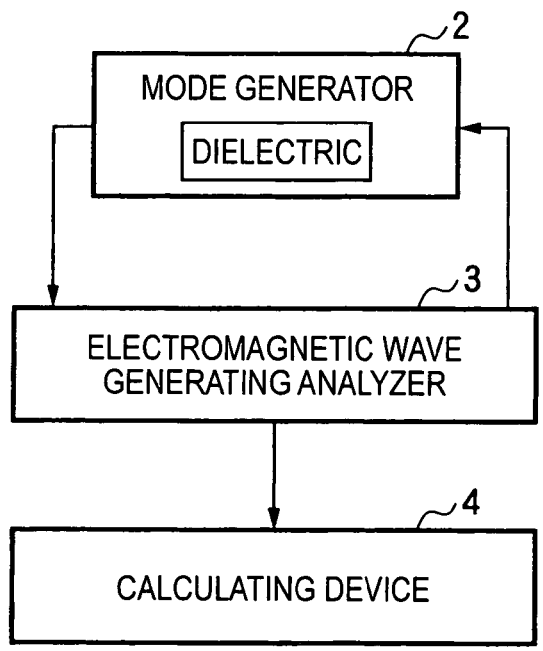
FIG. 1 is a block diagram schematically showing an apparatus for measuring the complex dielectric constant of a dielectric according to the invention.

FIG. 1 is a block diagram showing the schematic structure of an apparatus for measuring the complex dielectric constant of a dielectric according to the invention.

As shown in FIG. 1, a measuring apparatus 1 is constituted by a mode generator 2, an electromagnetic wave generating analyzer 3 and a calculating device 4.

The mode generator 2 is a container for holding, together with a gas, a dielectric of which complex dielectric constant is to be measured. The mode generator 2 can cause only a wave in a predetermined mode to be present for an electromagnetic wave which is input, and can use a resonator and a waveguide, for example. The dielectric filled in the mode generator 2 includes a powder-like dielectric, a molding formed by a single material which is obtained by burning the powder-like dielectric, and a molding formed by a plurality of materials which is obtained by mixing the powder-like dielectric and resin at various ratios.

The electromagnetic wave generating analyzer 3 inputs an electromagnetic wave into the mode generator 2 and receives the electromagnetic wave output from the mode generator 2 in response to the input electromagnetic wave. Then, the electromagnetic wave generating analyzer 3 analyzes the received electromagnetic wave, thereby calculating an S parameter of the electromagnetic wave in the mode generator 2 and outputting data on the calculated S parameter to the calculating device 4. The S parameter of the electromagnetic wave indicates a transmission coefficient and a reflection coefficient of the electromagnetic wave.

The calculating device 4 calculates the complex dielectric constant of the dielectric based on the S parameter input from the electromagnetic wave generating analyzer 3.

In the case in which the dielectric provided in the mode generator 2 is not the molding but a powder, the calculating device 4 cannot directly calculate the complex dielectric constant of the powder-like dielectric but first calculates the complex dielectric constant of a mixture containing the powder-like dielectric and air to obtain the complex dielectric constant of only the powder-like dielectric by using an equation of "Lichteneker Rother" or that of Wiener.

Thus, the apparatus for measuring the complex dielectric constant of a dielectric according to the invention has such a structure that an electromagnetic wave is input into the mode generator 2 and an analysis is carried out based on the electromagnetic wave which is output, thereby measuring the complex dielectric constant of the dielectric to be the powder or the molding.

Description will be given to a method for measuring the complex dielectric constant of a dielectric together with the more specific structure of the measuring apparatus.

First Embodiment

A first embodiment of the apparatus and method for measuring the complex dielectric constant of a dielectric according to the invention will be described below in detail. In the embodiment, a cavity resonator is used as the mode generator shown in FIG. 1.

Figure 2:
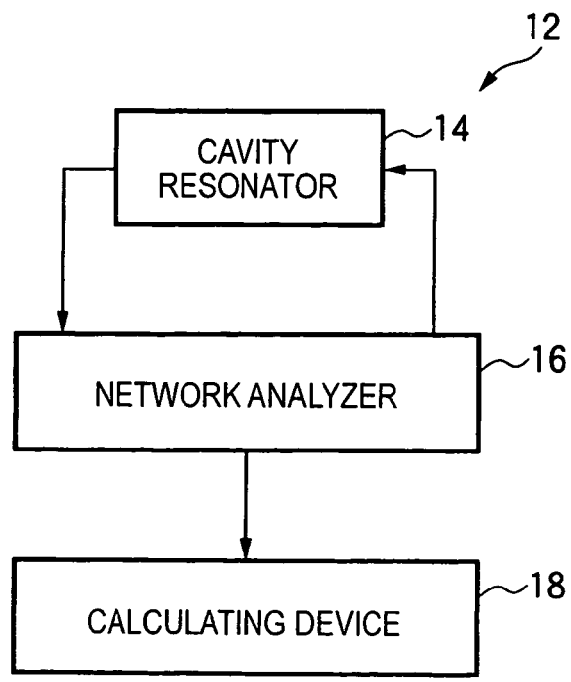
FIG. 2 is a block diagram showing an apparatus for measuring the complex dielectric constant of a dielectric according to a first embodiment of the invention.
Figure 3:
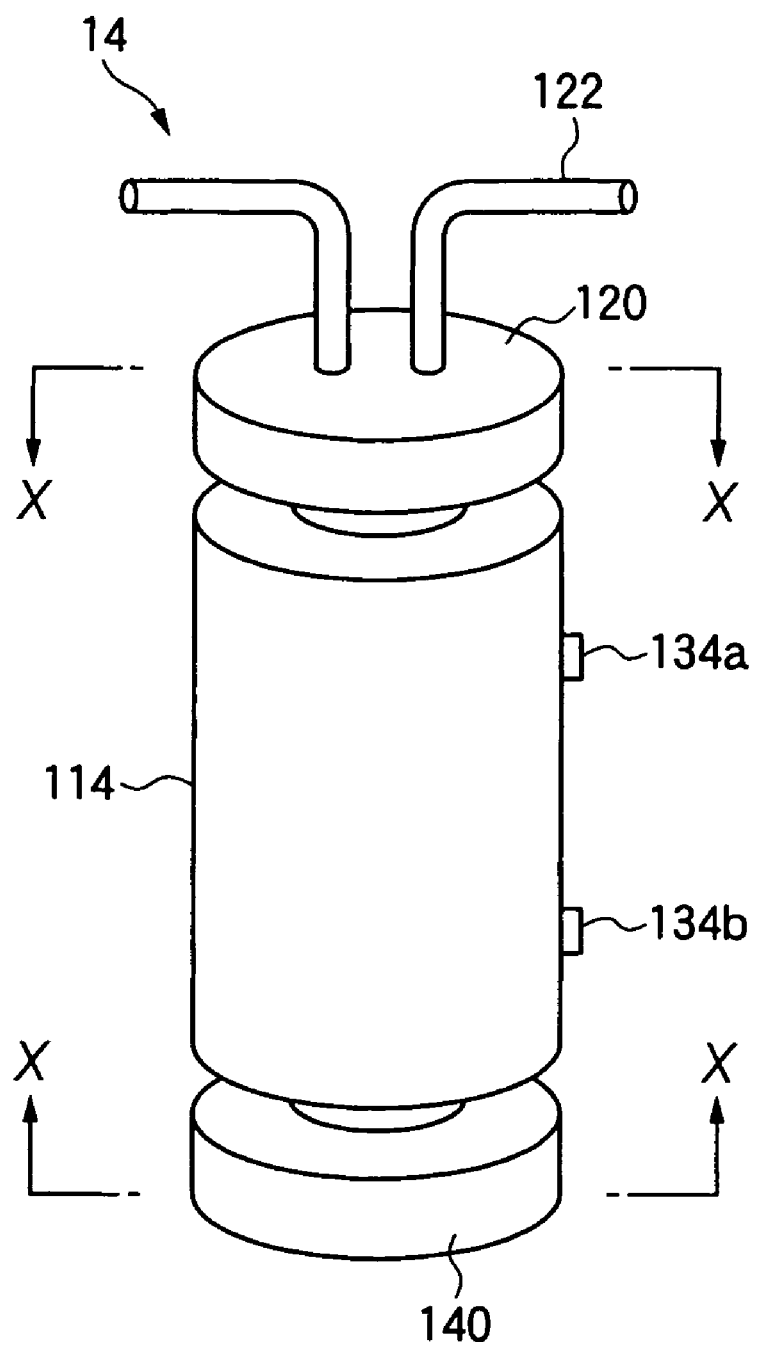
FIG. 3 is a schematic perspective view showing a cavity resonator.
Figure 4:
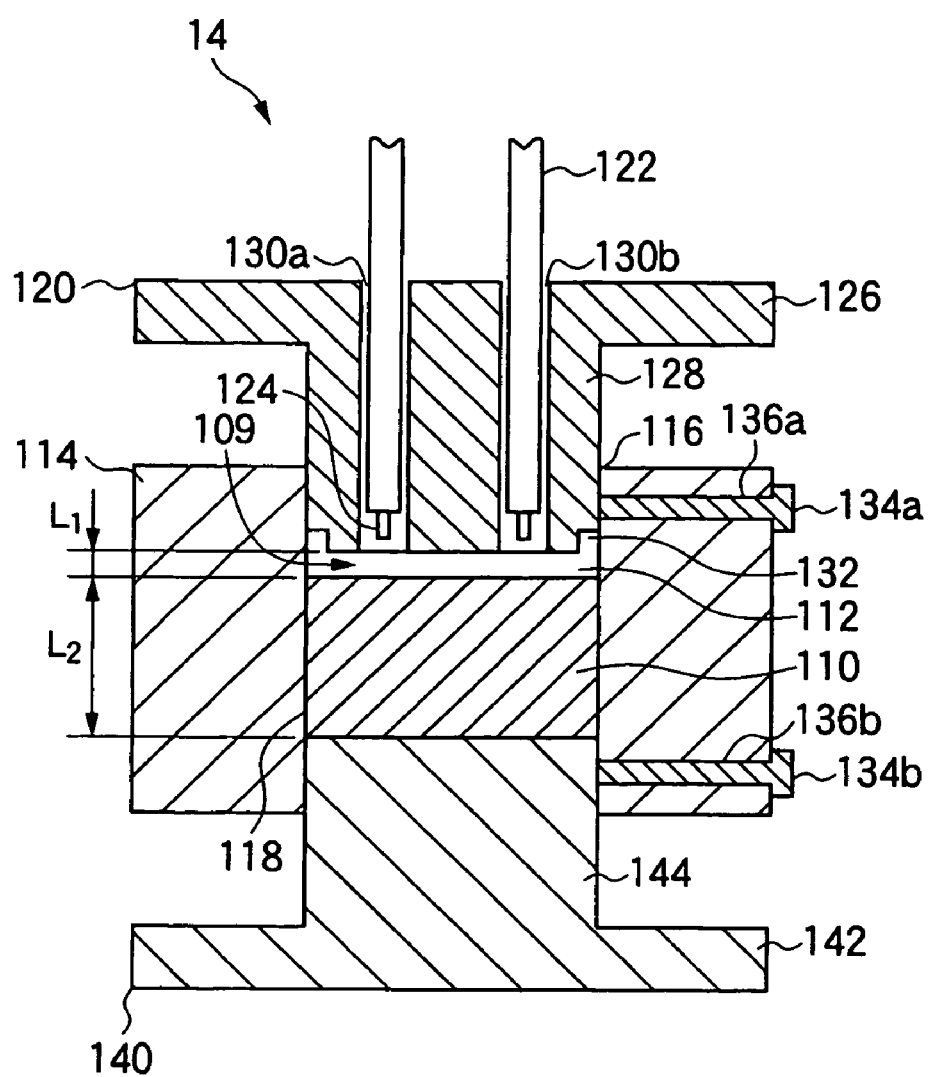
FIG. 4 is a schematic sectional view showing the cavity resonator illustrated in FIG. 2 which is taken along an X—X line, a powder-like dielectric being provided.

FIG. 2 is a block diagram showing the measuring apparatus for executing the method for measuring the complex dielectric constant of a dielectric according to the embodiment, FIG. 3 is a schematic perspective view showing the cavity resonator, and FIG. 4 is a schematic sectional view showing the cavity resonator illustrated in FIG. 3, which is taken along an X—X line, showing a powder-like dielectric as the dielectric.

As shown in FIG. 2, a measuring apparatus 12 comprises a cavity resonator 14, a network analyzer 16 and a calculating device 18 which correspond to the mode generator 2, the electromagnetic wave generating analyzer 3 and the calculating device 4 in FIG. 1 respectively in order. More specifically, the measuring apparatus 12 according to the embodiment applies the cavity resonator 14 as the mode generator 2.

The cavity resonator 14 is a cylindrical metallic container to be filled with a dielectric of which complex dielectric constant is to be measured. When an electromagnetic wave is input into the cavity resonator 14, an electromagnetic wave in a predetermined mode is strongly observed by a resonance corresponding to the shape of the cavity resonator 14.

The network analyzer 16 inputs an electromagnetic wave into the cavity resonator 14 and receives the electromagnetic wave output from the cavity resonator 14 in response to the input of the electromagnetic wave. Then, the network analyzer 16 measures a resonance frequency, an insertion loss and a half-power width of an electromagnetic wave in a predetermined mode from the electromagnetic wave received from the cavity resonator 14, thereby outputting a result of the measurement to the calculating device 18.

The calculating device 18 is constituted to calculate the complex dielectric constant of the dielectric from the resonance frequency, the insertion loss and the half-power width which are input from the network analyzer 16.

As shown in FIG. 3, the cavity resonator 14 includes a cylinder 114, a first piston 120, a coaxial cable 122, screws 134a and 134b, and a second piston 140.

As shown in FIG. 4, the first piston 120 has a first disk 126 and a first cylinder 128 erected integrally around the first disk 126. The first disk 126 and the first cylinder 128 are provided with two through holes 130a and 130b in the axial direction of the first cylinder 128. Moreover, an annular groove 132 is formed in the peripheral edge portion of the tip portion of the first cylinder 128.

As shown in FIG. 4, the coaxial cable 122 is inserted in the two through holes 130a and 130b formed on the first disk 126 and the first cylinder 128, and a loop antenna 124 is attached to the tip portion of the coaxial cable 122.

As shown in FIG. 4, the second piston 140 has a second disk 142 and a second cylinder 144 erected integrally around the second disk 142. The outside diameter of the second cylinder 144 is equal to that of the first cylinder 128.

As shown in FIG. 4, the central part of the cylinder 114 is provided with a through hole 116 having an inside diameter which is almost equal to the outside diameter of the first cylinder 128 of the first piston 120 and that of the second cylinder 144 of the second piston 140. The first cylinder 128 of the first piston 120 is inserted into the through hole 116 from above and the second cylinder 144 of the second piston 140 is inserted into the through hole 116 from below, and a closed space 109 is formed in the through hole 116 of the cylinder 114 by the first cylinder 128 of the first piston 120 and the second cylinder 144 of the second piston 140. The closed space 109 is a region to be the resonance cavity of the cavity resonator 14 and is filled with the powder-like dielectric or the dielectric molding which are to be measured together with the gas.

Moreover, the cylinder 114 is provided with two through holes 136a and 136b which are almost orthogonal to the axial direction of the cylinder 114. The screw 134a for adjusting the position of the first cylinder 128 of the first piston 120 is inserted in the through hole 136a, and the screw 134b for adjusting the position of the second cylinder 144 of the second piston 140 is inserted in the through hole 136b.

In the measuring apparatus 12 having the structure described above, the complex dielectric constant of the powder-like dielectric is measured in the following manner.

(Measurement of Complex Dielectric Constant of Powder-like Dielectric)

First of all, the measurement of the complex dielectric constant of the powder-like dielectric will be mainly described with reference to FIG. 4.

In order to measure the complex dielectric constant of the powder-like dielectric, first of all, a gas such as air, an argon gas or a nitrogen gas is filled in the closed space formed in the cavity resonator 14. In this state, the network analyzer 16 outputs an electromagnetic wave into the cavity resonator 14 through the coaxial cable 122 and the loop antenna 124.

The cavity resonator 14 excites the electromagnetic wave in a predetermined mode in response to the input of the electromagnetic wave. The excited electromagnetic wave is received by the loop antenna 124. The electromagnetic wave received by the loop antenna 124 is input to the network analyzer 16 through the coaxial cable 122.

The network analyzer 16 measures a resonance frequency $f_1$ in a $TE_{011}$ mode to be a resonance mode in the cavity resonator 14, an insertion loss $IL_1$ and a half-power width $\Delta f_1$ at the resonance frequency $f_1$, and a resonance frequency $f_2$ in a $TE_{012}$ mode based on the electromagnetic wave output from the cavity resonator 14.

In general, when the electromagnetic wave is input from the network analyzer 16 to the cavity resonator 14, a $TM_{111}$ mode is present as a degeneracy mode for the $TE_{011}$ mode. A resonance frequency in the $TM_{111}$ mode has a frequency band which is very close to the resonance frequency in the $TE_{011}$ mode. Therefore, there is a problem in that two peaks overlap with each other over a frequency spectrum which is measured and the resonance frequency, the insertion loss and the half-power width in the $TE_{011}$ mode cannot be measured accurately.

In order to solve this problem in the embodiment, however, the annular groove 132 is formed in the tip portion of the first cylinder 128 of the first piston 120, and furthermore, the closed space 109 is filled with a gas such as air, an argon gas or a nitrogen gas. Consequently, the resonance frequency in the $TE_{011}$ mode and the resonance frequency in the $TM_{111}$ mode in the cavity resonator 14 are separated from each other. By the separation of the resonance frequencies, the resonance frequency in the $TE_{011}$ mode is measured accurately.

The network analyzer 16 outputs, to the calculating device 18, the resonance frequency $f_1$ in the $TE_{011}$ mode, and the insertion loss $IL_1$ and the half-power width $\Delta f_1$ at the resonance frequency $f_1$ which are measured, and the resonance frequency $f_2$ in the $TE_{012}$ mode.

When the network analyzer 16 outputs, to the calculating device 18, the resonance frequency $f_1$ in the $TE_{011}$ mode, the insertion loss $IL_1$ and the half-power width $\Delta f_1$ at the resonance frequency $f_1$, and the resonance frequency $f_2$ in the $TE_{012}$ mode, the closed space 109 of the cavity resonator 14 is filled with a powder-like dielectric 110 of which complex dielectric constant is to be measured.

It is preferable that the powder-like dielectric 110 to be measured should be previously put in a vacuum or heating should be carried out to remove a moisture contained in the dielectric 110 to be dried.

In the measurement of the complex dielectric constant of the powder-like dielectric 110, generally, there is a problem in that an error is made in the measurement of the complex dielectric constant of the powder-like dielectric 110 by the influence of the moisture adsorbed onto the surface of the powder-like dielectric 110. In the structure, however, the moisture of the powder-like dielectric 110 to be measured is previously removed and the complex dielectric constant of the powder-like dielectric 110 is then measured. Consequently, it is possible to enhance precision in the measurement of the complex dielectric constant of the powder-like dielectric 110.

When the closed space 109 of the cavity resonator 14 is filled with the powder-like dielectric 110, a layer 112 of a gas such as the air, the argon gas or the nitrogen gas and a layer 118 of a mixture obtained by mixing the powder-like dielectric 110 and the air are formed in the closed space 109 of the cavity resonator 14 as shown in FIG. 4.

Subsequently, the network analyzer 16 outputs the electromagnetic wave through the coaxial cable 122 and the loop antenna 124 to the cavity resonator 14 filled with the powder-like dielectric 110 of which complex dielectric constant is to be measured.

When the network analyzer 16 inputs the electromagnetic wave into the cavity resonator 14, the electromagnetic wave is output from the cavity resonator 14 and is received by the loop antenna 124 in response to the input of the electromagnetic wave. The electromagnetic wave received by the loop antenna 124 is input to the network analyzer 16 through the coaxial cable 122.

The network analyzer 16 analyzes the input electromagnetic wave to calculate a resonance frequency $f_3$ in the $TE_{011}$ mode of the resonance mode, and an insertion loss $IL_3$ and a half-power width $\Delta f_3$ at the resonance frequency $f_3$. Then, the network analyzer 16 outputs, to the calculating device 18, data on the resonance frequency $f_3$ in the $TE_{011}$ mode, and the insertion loss $IL_3$ and the half-power width $\Delta f_3$ at the resonance frequency $f_3$.

The calculating device 18 calculates an effective conductivity $\sigma$ of the internal wall of the cavity resonator 14, $Q_1$ to be a unload Q value of the cavity resonator 14 in a state in which the closed space 109 of the cavity resonator 14 is filled with the powder-like dielectric 110, and an apparent diameter D of the closed space 109 of the cavity resonator 14 by using the following Equations (1) to (3) based on the resonance frequency $f_1$, the insertion loss $IL_1$, the half-power width $\Delta f_1$ and the resonance frequency $f_2$ which are input from the network analyzer 16.

[Equation 1]

$$D = \frac{c}{\pi}\sqrt{\frac{j'^2_{n_2 m_2} \cdot l_1^2 - j'^2_{n_1 m_1} \cdot l_2^2}{f_2^2 \cdot l_1^2 - f_1^2 \cdot l_2^2}} \quad (1)$$

$$H = \frac{c}{2}\sqrt{\frac{j'^2_{n_2 m_2} \cdot l_1^2 - j'^2_{n_1 m_1} \cdot l_2^2}{f_1^2 \cdot j'^2_{n_2 m_2} - f_2^2 \cdot j'^2_{n_1 m_1}}}$$

: an apparent height of the closed space,

D: an apparent diameter of the closed space, $j'_{n_1 m_1}$: an m1st solution to be $j'_{n_1}(x)=0$ when a differential of an n1-order first kind Bessel function is set to be $j'_{n_1}(x)$, $j'_{n_2 m_2}$: an m2nd solution to be $j'_{n_2}(x)=0$ when a differential of an n2-order first kind Bessel function is set to be $j'_{n_2}(x)$, and c: a light velocity in a vacuum.

[Equation 2]

$$Q_1 = \frac{f_1/\Delta f_1}{1 - 10^{-IL_1/20}} \quad (2)$$

$f_1$: a resonance frequency, $\Delta f_1$: a half-power width, and $IL_1$: an insertion loss.

[Equation 3]

$$\sigma = \frac{4\pi f_1 Q_1^2 \left\{ j'^4_{n_1 m_1} + 2(j'_{n_1 m_1} l_1 \pi)^2 \left(\frac{D}{2H}\right)^3 + \left(1 - \frac{D}{H}\right)\left(\frac{n_1 l_1 \pi D}{2H}\right)^2 \right\}}{\mu_0 c^2 (j'^2_{n_1 m_1} - n_1^2)^2 \left\{ j'^2_{n_1 m_1} + \left(\frac{l_1 \pi D}{2H}\right)^2 \right\}^3}$$ (3)

σ: an effective conductivity of the internal wall of the cavity resonator, $\mu_0$: a permeability in a vacuum, and π: a circular constant.

Next, the calculating device 18 substitutes, for Equations (4) and (5), the resonance frequency $f_3$, the half-power width $\Delta f_3$, and the insertion loss $IL_3$ which are input from the network analyzer 16, the apparent diameter D of the closed space 109 of the cavity resonator 14 which has already been obtained, a thickness $L_1$ of the layer 112 of the gas filled in the closed space 109, and a thickness $L_2$ of the layer 118 of a mixture obtained by mixing the powder-like dielectric 110 and the gas, and calculates $Q_3$ to be an unload Q value of the cavity resonator 14 in a state in which the cavity resonator 14 is filled with the powder-like dielectric 110 and a dielectric constant $\in_{r2}$ in the complex dielectric constant of the layer 118 of the mixture obtained by mixing the powder-like dielectric 110 and the gas.

The thickness $L_1$ of the layer 112 of the gas and the thickness $L_2$ of the layer 118 of the mixture obtained by mixing the powder-like dielectric 110 and the gas have preset values, and are set by a measuring person and are then input to the calculating device 18.

[Equation 4]

$$Q_3 = \frac{f_3/\Delta f_3}{1 - 10^{-IL_3/20}}$$ (4)

$f_3$: resonance frequency, $\Delta f_3$: half-power width, and $IL_3$: insertion loss.

[Equation 5]

$$\begin{aligned} L_1 \frac{\tan X_1}{X_1} + L_2 \frac{\tan X_2}{X_2} &= 0 \\ X_1 &= \beta_1 L_1 \\ X_2 &= \beta_2 L_2 \\ \beta_1 &= \sqrt{\varepsilon_{r1} k_0^2 - k_r^2} \\ \beta_2 &= \sqrt{\varepsilon_{r2} k_0^2 - k_r^2} \\ k_r &= \frac{2 j'_{nm}}{D} \\ k_0 &= \frac{2\pi f_3}{c} \end{aligned}$$ (5)

$L_1$: a thickness of the layer 112 of the gas, $L_2$: a thickness of the layer 118 of the mixture obtained by mixing the powder-like dielectric 110 and the gas, D: an apparent diameter of the closed space 109, $\in_{r1}$: a dielectric constant of the gas, $\in_{r2}$: a dielectric constant of the layer 118 of the mixture obtained by mixing the powder-like dielectric 110 and the gas, and $j'_{nm}$: an mth solution to be $j'_n(x)=0$ when a differential of an n-order first kind Bessel function is set to be $j'_n(x)$.

Subsequently, the calculating device 18 substitutes, for Equation (6), the effective conductivity σ which has already been calculated, $Q_3$ to be the unload Q value of the cavity resonator 14 in the state in which the cavity resonator 14 is filled with the powder-like dielectric 110, the apparent diameter D of the closed space 109, the thickness $L_1$ of the layer 112 of the gas filled in the closed space 109, and the thickness $L_2$ of the layer 118 of the mixture obtained by mixing the powder-like dielectric 110 and the gas, and calculates a dielectric loss tangent in the complex dielectric constant of the layer 118 of the mixture obtained by mixing the powder-like dielectric 110 and the gas.

[Equation 6]

$$\begin{aligned} \tan \delta &= \frac{A}{Q_3} - R_s B \\ A &= 1 + \frac{W_{e1}}{W_{e2}} \\ B &= \frac{P_{cy1} + P_{cy2} + P_{end1} + P_{end2}}{2\omega W_{e2} R_s} \\ W_{e1} &= \frac{1}{8} \varepsilon_{r1} \varepsilon_0 \omega^2 \mu_0^2 j'^2_{01} J_0^2(j'_{01}) \pi L_1 \left(1 - \frac{\sin 2X_1}{2X_1}\right) \\ W_{e2} &= \frac{1}{8} \varepsilon_{r2} \varepsilon_0 \omega^2 \mu_0^2 j'^2_{01} J_0^2(j'_{01}) \pi L_2 \left(1 - \frac{\sin 2X_2}{2X_2}\right) \frac{\sin^2 X_1}{\sin^2 X_2} \\ P_{cy1} &= \frac{1}{4} R_s k_r^4 J_0^2(j'_{01}) D \pi L_1 \left(1 - \frac{\sin 2X_1}{2X_1}\right) \\ P_{cy2} &= \frac{1}{4} R_s k_r^4 J_0^2(j'_{01}) D \pi L_2 \left(1 - \frac{\sin 2X_2}{2X_2}\right) \frac{\sin^2 X_1}{\sin^2 X_2} \\ P_{end1} &= \frac{1}{2} R_s \left(\frac{X_1}{L_1}\right)^2 j'^2_{01} \pi J_0^2(j'_{01}) \\ P_{end2} &= \frac{1}{2} R_s \left(\frac{X_2}{L_2}\right)^2 j'^2_{01} \pi J_0^2(j'_{01}) \frac{\sin^2 X_1}{\sin^2 X_2} \\ R_s &= \sqrt{\frac{\pi f_3 \mu_0}{\sigma}} \\ \omega &= 2\pi f_3 \end{aligned}$$ (6)

$Q_3$: an unload Q value of the cavity resonator 14 in the state in which the cavity resonator 14 is filled with the powder-like dielectric 110, $W_{e1}$: a stored energy of an electric field of the layer 112 of the gas, $W_{e2}$: a stored energy of an electric field of the layer 118 of the mixture obtained by mixing the powder-like dielectric 110 and the gas, $P_{cy1}$: a conductor loss in the side wall of the layer 112 of the gas, $P_{cy2}$: a conductor loss in the side wall of the layer 118 of the mixture obtained by mixing the powder-like dielectric 110 and the gas, $P_{end1}$: a conductor loss on the piston end face of the layer 112 of the gas, $P_{end2}$: a conductor loss on the piston end face of the layer 118 of the mixture obtained by mixing the powder-like dielectric 110 and the gas, $\omega$: angular frequency, $R_s$: a surface resistance of the internal wall of the cavity resonator 14, and $j'_{01}$: a first solution to be $j'_0(x)=0$ when a differential of a 0-order first kind Bessel function is set to be $j'_0(x)$.

By the foregoing, the dielectric constant $\epsilon_{r2}$ and the dielectric loss tangent are calculated as the complex dielectric constant of the layer 118 of the mixture obtained by mixing the powder-like dielectric 110 and the gas.

Furthermore, the calculating device 18 applies the dielectric constant $\epsilon_{r2}$ of the layer 118 of the mixture obtained by mixing the powder-like dielectric 110 and the gas which is thus calculated to an equation for calculating a dielectric constant $\epsilon_r$ of the powder-like dielectric from the dielectric constant $\epsilon_{r2}$ of the layer 118 of the mixture obtained by mixing the powder and the gas, for example, a logarithmic alligation, the equation of "Lichteneker Rother" or the equation of Wiener, thereby calculating the dielectric constant $\epsilon_r$ of the powder-like dielectric 110.

As is well-known, the logarithmic alligation is expressed in the following equation.

$$\log \epsilon_r = v_1 \log \epsilon_{r1} + v_2 \log \epsilon_{r2}$$

Moreover, the equation of "Lichteneker Rother" is expressed in the following equation.

$$\epsilon_r^k = v_1 \epsilon_{r1}^k + v_2 \epsilon_{r2}^k$$

On the other hand, the equation of Wiener is expressed in the following equation.

$$1/(\epsilon_r + u) = v_1/(\epsilon_{r1} + u) + v_2/(\epsilon_{r2} + u)$$

$\epsilon_r$: a dielectric constant of a powder-like dielectric, $\epsilon_{r1}$: a dielectric constant of a gas, $\epsilon_{r2}$: a dielectric constant of the layer 118 of a mixture obtained by mixing the powder-like dielectric 110 and the gas, $v_1$: a volume ratio of the gas, $v_2$: a volume ratio of the powder-like gas, k: fitting parameter ($-1 \leq k \leq 1$), and u: fitting parameter ($0 \leq u$)

By these equations, the dielectric constant $\epsilon_r$ of the powder-like dielectric is calculated.

For example, in the case in which the dielectric constant $\epsilon_r$ of the powder-like dielectric 110 is to be calculated from the dielectric constant $\epsilon_{r2}$ of the layer 118 of the mixture obtained by mixing the powder-like dielectric 110 and the air by using the air as the gas, the dielectric constant $\epsilon_{r1}$ of the air is 1.0. Moreover, the volume ratio $v_1$ of the air and the volume ratio $v_2$ of the powder-like dielectric are determined by the volume of the air filled in the layer 118 of the mixture and that of the powder-like dielectric 110. If the dielectric constant $\epsilon_{r2}$ of the layer 118 of the mixture obtained by mixing the powder-like dielectric 110 and the air is obtained, therefore, the dielectric constant $\epsilon_r$ of the powder-like dielectric 110 can be calculated.

Furthermore, the calculating device 18 applies the dielectric loss tangent of the layer 118 of the mixture obtained by mixing the powder-like dielectric 110 and the gas which is thus calculated to the equation for calculating the dielectric loss tangent of the layer 118 of the mixture obtained by mixing the powder-like dielectric 110 and the gas from the dielectric loss tangent of the layer 118 of the mixture obtained by mixing the powder and the gas, that is, the equation of an alligation, thereby calculating the dielectric loss tangent of the powder-like dielectric 110.

The alligation for calculating the dielectric loss tangent is expressed in the following equation.

$$\tan \delta = v_1 \tan \delta_1 + v_2 \tan \delta_2$$

$\tan \delta$: a dielectric loss tangent of a powder-like dielectric, $\tan \delta_1$: a dielectric loss tangent of a gas, $\tan \delta_2$: a dielectric loss tangent of the layer 118 of the mixture obtained by mixing the powder-like dielectric 110 and the gas, $v_1$: a volume ratio of the gas, and $v_2$: a volume ratio of the powder-like dielectric.

By these equations, the dielectric loss tangent of the powder-like dielectric is calculated.

For example, in the case in which the dielectric loss tangent of the powder-like dielectric 110 is to be calculated from the dielectric loss tangent of the layer 118 for the mixture obtained by mixing the powder-like dielectric 110 and the air by using the air as a gas, the dielectric loss tangent $\tan \delta_1$ of the air can be regarded to be zero, and furthermore, the volume ratio $v_2$ of the powder-like dielectric 110 is determined by the volume of the gas filled in the layer 118 of the mixture and the volume of the powder-like dielectric 110. If the dielectric loss tangent $\tan \delta_2$ of the layer 118 of the mixture obtained by mixing the powder-like dielectric 110 and the air is obtained, therefore, the dielectric loss tangent of the powder-like dielectric 110 can be calculated.

As described above, the dielectric constant $\epsilon_r$ and the dielectric loss tangent of the powder-like dielectric 110 are obtained. As a result, the complex dielectric constant of the powder-like dielectric 110 can be obtained.

In the embodiment, in the case in which the dielectric constant of the complex dielectric constant of the dielectric is to be measured in the high frequency band of several GHz or more, the cavity resonator 14 is filled with the powder-like dielectric and the gas, the electromagnetic wave is input from the network analyzer 16 into the cavity resonator 14, the resonance frequency $f_3$, the half-power width $\Delta f_3$ and the insertion loss $IL_3$ in the TE mode of the electromagnetic wave input to the network analyzer 16 from the cavity resonator 14 to which the electromagnetic wave is input are measured, the dielectric constant $\in_{r2}$ of the layer 118 of the mixture obtained by mixing the powder-like dielectric 110 and the gas is calculated, and furthermore, the dielectric constant $\in_{r2}$ of the layer 118 of the mixture obtained by mixing the powder-like dielectric 110 and the gas which is calculated is applied to the equation for calculating the dielectric constant $\in_r$ of the powder-like dielectric 110 from the dielectric constant $\in_{r2}$ of the layer 118 of the mixture obtained by mixing the powder-like dielectric 110 and the gas, for example, the logarithmic alligation, the equation of "Lichteneker Rother" or the equation of Wiener, thereby calculating the dielectric constant $\in_r$ of the powder-like dielectric 110.

According to the structure, therefore, the dielectric constant in the complex dielectric constant of the powder-like dielectric 110 can be measured with high precision also in the high frequency band of several GHz or more.

In the structure, moreover, in the case in which the dielectric loss tangent of the complex dielectric constant of the dielectric is to be measured in the high frequency band of several GHz or more, the cavity resonator 14 is filled with the powder-like dielectric and the gas, the electromagnetic wave is input from the network analyzer 16 into the cavity resonator 14, the resonance frequency $f_3$ the half-power width $\Delta f_3$ and the insertion loss $IL_3$ in the TE mode of the electromagnetic wave input to the network analyzer 16 from the cavity resonator 14 to which the electromagnetic wave is input are measured and the dielectric loss tangent of the layer 118 of the mixture obtained by mixing the powder-like dielectric 110 and the gas is calculated, and furthermore, is applied to the equation of an alligation for calculating the dielectric loss tangent of the powder-like dielectric from the dielectric loss tangent of the layer 118 of the mixture obtained by mixing the powder-like dielectric 110 and the gas, thereby calculating the dielectric loss tangent of the powder-like dielectric 110.

According to the embodiment, therefore, the dielectric loss tangent in the complex dielectric constant of the powder-like dielectric 110 can be measured with high precision also in the high frequency band of several GHz or more.

(Measurement of Complex Dielectric Constant of Dielectric Molding)

Next, the measurement of the complex dielectric constant of a dielectric molding will be mainly described with reference to FIG. 5. Description will be given to the case in which a dielectric is formed cylindrically to measure the complex dielectric constant. In the following description, the same portions as those in the measurement of the complex dielectric constant of a powder-like dielectric will be omitted below by using simple description, and furthermore, characters having finely different definition which are similar to those in the powder-like dielectric will be redefined and the same characters will be used therefor.

In order to measure the complex dielectric constant of a dielectric molding, in the same manner as in the case in which the powder-like dielectric is to be measured, first of all, a gas such as air, an argon gas or a nitrogen gas is filled in the closed space 109 formed in the cavity resonator 14, and an electromagnetic wave is input from the network analyzer 16 into the closed space 109 in this state, the output of the electromagnetic wave input into the closed space 109 is analyzed to measure the resonance frequency $f_1$ in the $TE_{011}$ mode, the insertion loss $IL_1$ and the half-power width $f_1$ at the resonance frequency $f_1$, and the resonance frequency $f_2$ in the $TE_{012}$ mode.

Then, a cylindrical dielectric molding 110A of which complex dielectric constant is to be measured is filled in the closed space 109 of the cavity resonator 14. The diameter of the section of the cylindrical dielectric molding 110A is set to be equal to the inside diameter of the through hole 116.

Figure 5:
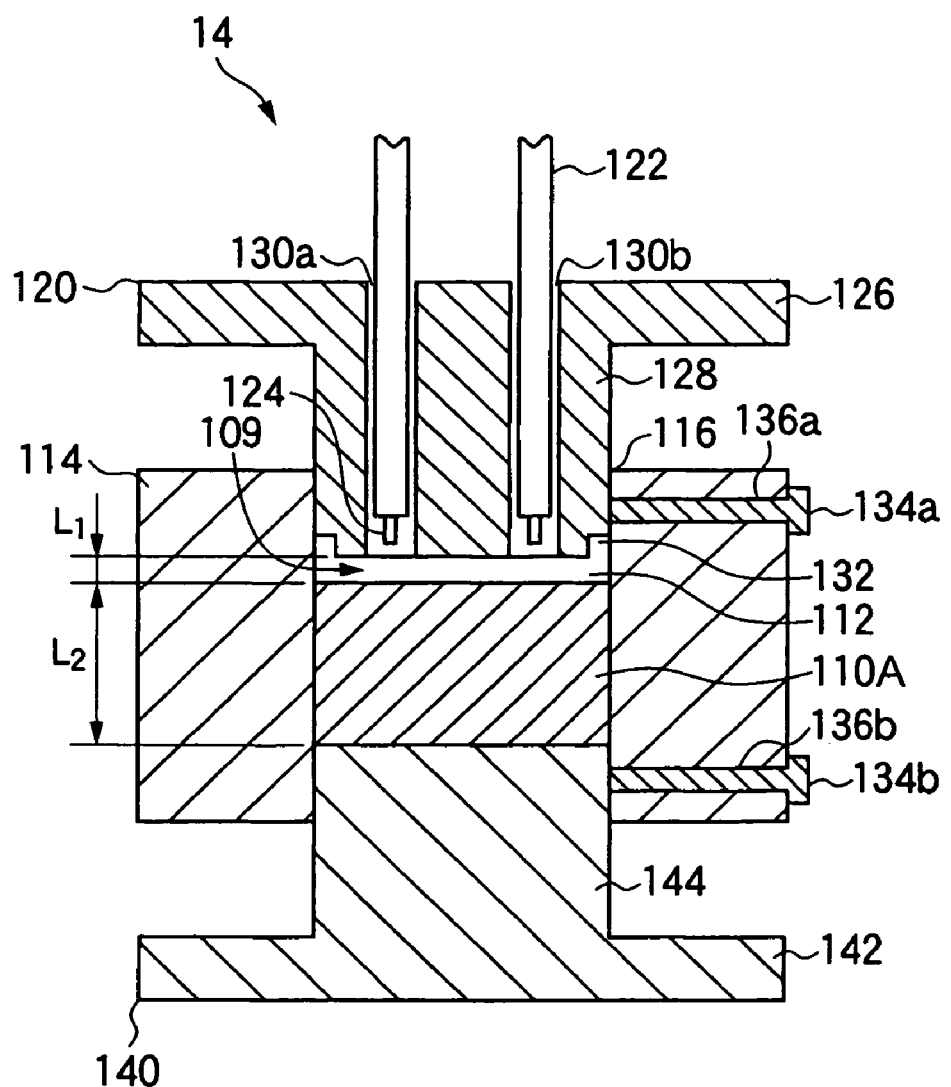
FIG. 5 is a schematic sectional view showing the cavity resonator illustrated in FIG. 2 which is taken along the X—X line, a dielectric molding being provided.

As a result, as shown in FIG. 5, the layer 112 of a gas such as the air, the argon gas or the nitrogen gas is formed in the closed space 109 of the cavity resonator 14.

In the same manner as in the case of the powder-like molding 110, next, an electromagnetic wave is output from the network analyzer 16 into the closed space 109 through the coaxial cable 122 and the loop antenna 124 in the cavity resonator 14 filled with the cylindrical dielectric molding 110A of which complex dielectric constant is to be measured, and the electromagnetic wave is received from the closed space 109 through the loop antenna 124 and is output to the network analyzer 16.

Subsequently, the network analyzer 16 calculates the resonance frequency $f_3$ in the $TE_{011}$ mode, and the insertion loss $IL_3$ and the half-power width $\Delta f_3$ at the resonance frequency $f_3$ from the electromagnetic wave output from the closed space 109.

Then, the calculating device 18 substitutes the resonance frequency $f_1$, the insertion loss $IL_1$, the half-power width $\Delta f_1$ and the resonance frequency $f_2$ which are input from the network analyzer 16 for the Equations (1) to (3) and calculates the effective conductivity σ of the internal wall of the cavity resonator 14, $Q_1$ to be the unload Q value of the cavity resonator 14 in a state in which the closed space 109 of the cavity resonator 14 is not filled with the cylindrical dielectric molding 110A, and the apparent diameter D of the closed space 109 of the cavity resonator 14.

Next, the calculating device 18 substitutes, for the Equations (4) and (5), the resonance frequency $f_3$, the half-power width $\Delta f_3$, and the insertion loss $IL_3$ which are input from the network analyzer 16, the apparent diameter D of the closed space 109 of the cavity resonator 14 which has already been obtained, the thickness $L_1$ of the layer 112 of the gas filled in the closed space 109, and the thickness $L_2$ of the cylindrical dielectric molding 110A, and calculates $Q_3$ to be the unload Q value of the cavity resonator 14 in a state in which the cavity resonator 14 is filled with the cylindrical dielectric molding 110A and the dielectric constant $\in_{r2}$ in the complex dielectric constant of the cylindrical dielectric molding 110A.

The thickness $L_1$ of the layer 112 of the gas and the thickness $L_2$ of the cylindrical dielectric molding 110A have preset values and are set by a measuring person, and are then input to the calculating device 18.

Subsequently, the calculating device 18 substitutes, for the Equation (6), the effective conductivity σ which has already been calculated, $Q_3$ to be the unload Q value of the cavity resonator 14 in the state in which the cavity resonator 14 is filled with the cylindrical dielectric molding 110A, the apparent diameter D of the closed space 109, the thickness $L_1$ of the layer 112 of the gas filled in the closed space 109, and the thickness $L_2$ of the cylindrical dielectric molding 110A, and calculates a dielectric loss tangent in the complex dielectric constant of the cylindrical dielectric molding 110A.

As described above, the dielectric constant $\epsilon_{r2}$ and the dielectric loss tangent of the cylindrical dielectric molding 110A are obtained. As a result, the complex dielectric constant of the cylindrical dielectric molding 110A can be obtained. Differently from the powder-like dielectric 110, when the dielectric is a molding, it is possible to directly obtain the complex dielectric constant of the dielectric by using the Equations (1) to (6).

As described above, in the embodiment, the cavity resonator 14 is filled with the cylindrical dielectric molding 110A and the gas, an electromagnetic wave is input from the network analyzer 16 into the cavity resonator 14, and the resonance frequency $f_3$, the half-power width $\Delta f_3$ and the insertion loss $IL_3$ in the TE mode of the electromagnetic wave input to the network analyzer 16 from the cavity resonator 14 to which the electromagnetic wave is input are measured to calculate the complex dielectric constant of the cylindrical dielectric molding 110A.

According to the embodiment, therefore, the complex dielectric constant of the cylindrical dielectric molding 110A can be measured with high precision.

For the structures shown in FIGS. 2 to 5, the following variant can be proposed.

Figure 6:
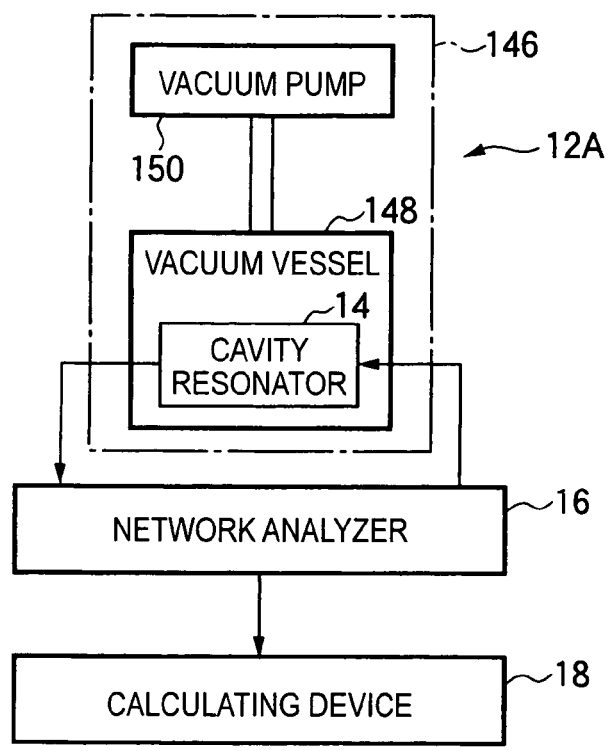
FIG. 6 is a diagram representing an apparatus for measuring the complex dielectric constant of a powder-like dielectric which includes a vacuum device for causing the closed space of the cavity resonator to be vacuum.

FIG. 6 is a diagram illustrating an apparatus 12A for measuring the complex dielectric constant of the powder-like dielectric 110 or the dielectric molding 110A which includes a vacuum device for causing the closed space 109 of the cavity resonator 14 to be vacuum.

In the variant, the cavity resonator 14 is covered with a vacuum device 146. The vacuum device 146 includes a vacuum vessel 148 and a vacuum pump 150. The vacuum vessel 148 is caused to be vacuum by using the vacuum pump 150 connected thereto. The cavity resonator 14 is provided in the vacuum vessel 148 and the inner part of the vacuum vessel 148 is brought into a vacuum condition so that the closed space 109 of the cavity resonator 14 is also brought into the vacuum condition.

In the variant, the cavity resonator 114 is filled with the powder-like dielectric 110 or the dielectric molding 110A and the inner part of the cavity resonator 14 is then brought into the vacuum condition by using the vacuum device 146. Consequently, it is possible to remove a moisture contained in the powder-like dielectric 110 or the dielectric molding 110A. By measuring the complex dielectric constant of the powder-like dielectric 110 or the dielectric molding 110A filled in the cavity resonator 14 in a state in which the moisture contained in the powder-like dielectric 110 or the dielectric molding 110A is removed, it is possible to enhance precision in the measurement of the complex dielectric constant of the powder-like dielectric 110 or the dielectric molding 110A.

Second Embodiment

A second embodiment of an apparatus and method for measuring the complex dielectric constant of a dielectric according to the invention will be described below in detail. In the embodiment, a waveguide is used as the mode generator shown in FIG. 1.

Figure 7:
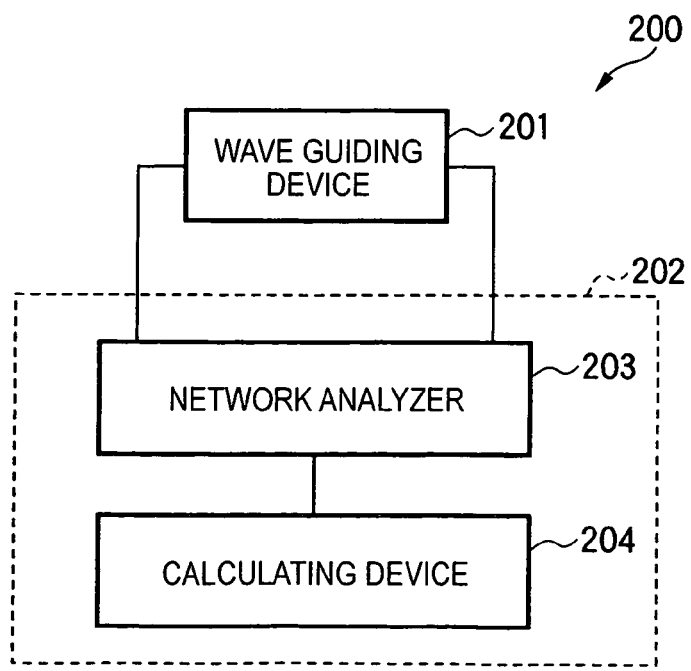
FIG. 7 is a block diagram showing the structure of a dielectric characteristic measuring apparatus 100 according to a second embodiment of the invention.
Figure 8:
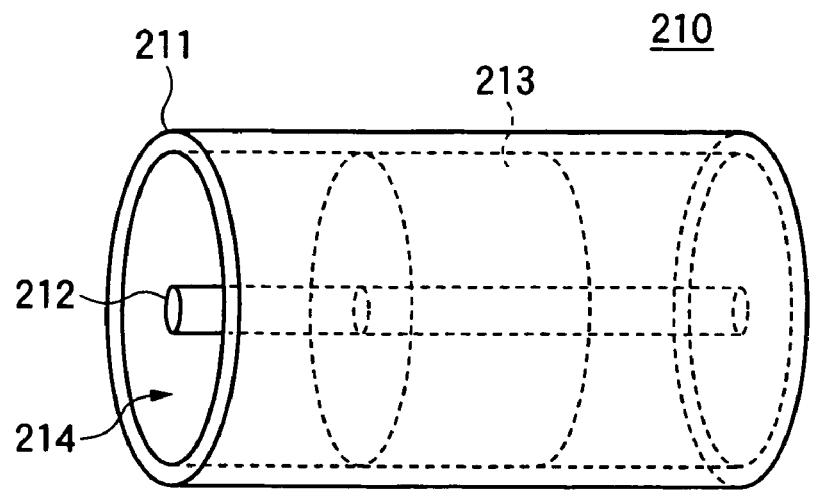
FIG. 8 is a perspective view showing a waveguide.
Figure 9:
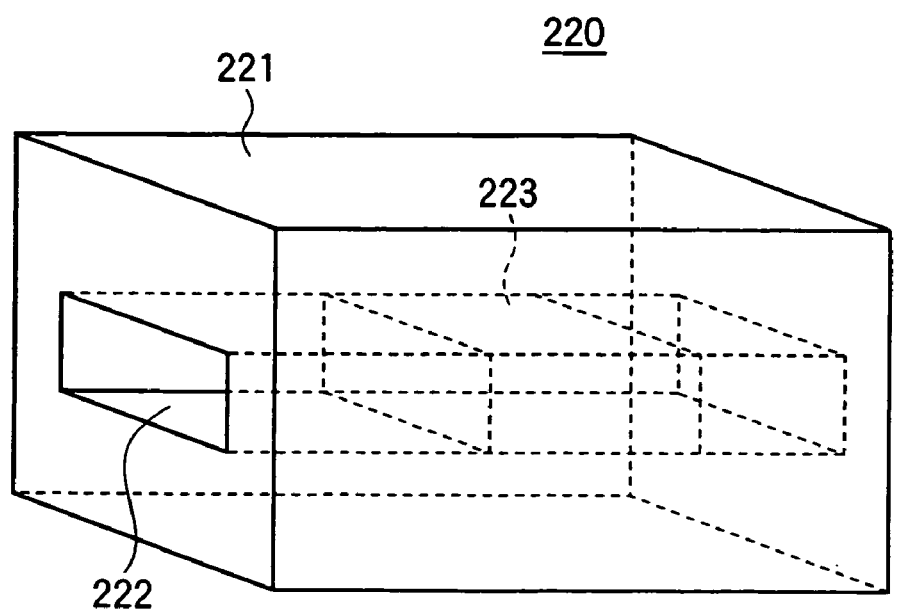
FIG. 9 is a perspective view showing the waveguide.
Figure 10:
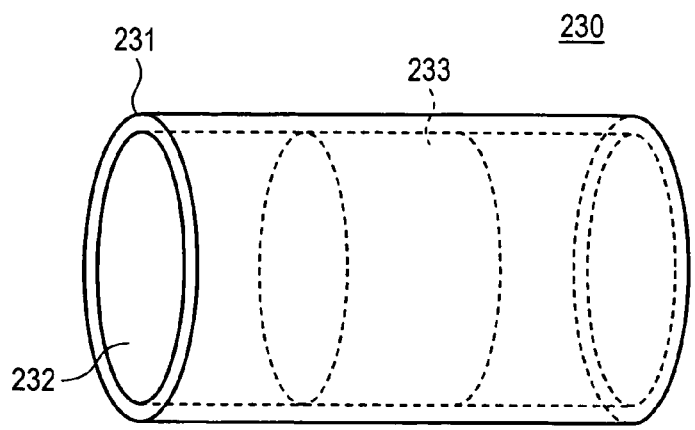
FIG. 10 is a perspective view showing the waveguide.

FIG. 7 is a block diagram showing the structure of the measuring apparatus according to the embodiment, and FIGS. 8 to 10 are views showing the waveguide, respectively.

As shown in FIG. 7, a dielectric characteristic measuring apparatus 200 comprises a wave-guiding device 201 and a measuring device 202.

The wave-guiding device 201 is applied as the mode generator shown in FIG. 1 and is constituted by waveguides 210, 220 and 230 for propagating a so-called electromagnetic wave shown in FIGS. 8 to 10.

The waveguide 210 shown in FIG. 8 is of a so-called coaxial type, and is constituted by a cylindrical external conductor 211 having an inner part to be a cavity, and a cylindrical central conductor 212 provided coaxially in the external conductor 211. In the embodiment, a mixture 213 of a powder to be a measuring object and a gas or liquid is filled in a gap 214 between the external conductor 211 and the central conductor 212.

Moreover, the waveguide 220 shown in FIG. 9 is of a so-called rectangular type, and is constituted by a conductor 221 including a gap 222 taking a rectangular shape seen in a section. A mixture 223 having a powder to be a measuring object and a gas or liquid is put in the gap 222 and is thus filled in the waveguide 220.

Furthermore, the waveguide 230 shown in FIG. 10 is of a so-called circular type, and is constituted by a cylindrical external conductor 231 including a gap 232 taking a circular shape seen in a section. A mixture 233 having the powder to be the measuring object and the liquid or gas is put in the gap 232 and is thus filled in the circular waveguide type waveguide 230.

In the case in which the dielectric constant of the mixture 213 having a gas other than air or a liquid and a powder is to be measured by using the same gas or liquid, the waveguides 210, 220 and 230 are provided with a seal portion (not shown) for holding the gas or liquid in the waveguides 210, 220 and 230 in order to prevent the gas or liquid from flowing out of the gaps 214, 222 and 232, respectively.

Returning to FIG. 7 again, description will be given.

The measuring device 202 includes a network analyzer 203 and a calculating device 204. The measuring device 202 excites the waveguide 201 and analyzes the output signal of the wave-guiding device 201.

The network analyzer 203 generates an electromagnetic wave to be input to the wave-guiding device 201 constituted by a waveguide and digitally processes analog data supplied from the wave-guiding device 201.

Moreover, the calculating device 204 fetches digital data supplied from the network analyzer 203 and carries out a processing for measuring and outputting a dielectric characteristic.

Next, description will be given to a dielectric characteristic measuring method using the dielectric characteristic measuring apparatus 200. A high-frequency electromagnetic wave is incident from the network analyzer 203 onto the wave-guiding device 201 to excite the wave-guiding device 201. Then, the transmitted wave and reflected wave of the wave-guiding device 201 are supplied to the network analyzer 203. Output data sent from the network analyzer 203 are fetched into the calculating device 204 to calculate the dielectric constant of the mixture filled in the wave-guiding device 201.

Then, the calculating device 204 applies a dielectric constant $\in$ of the composite containing the powder and the gas or liquid which is thus obtained to an equation for calculating the dielectric constant of a mixed material, for example, a logarithmic alligation, an equation of "Lichteneker Rother" or an equation of Wiener, thereby calculating the dielectric constant of the powder.

These equations will be described.

The logarithmic alligation is expressed in the following equation.

$$\log \in = v_1 \log \in_1 + v_2 \log \in_2$$

Moreover, the equation of "Lichteneker Rother" is expressed in the following equation.

$$\in^k = v_1 \in_1^k + v_2 \in_2^k$$

Furthermore, the equation of Wiener is expressed in the following equation.

$$1/(\in + u) = v_1/(\in_1 + u) + v_2/(\in_2 + u)$$

$\in$: a dielectric constant of a mixture, $\in_1$: a dielectric constant of a gas or liquid, $\in_2$: a dielectric constant of a powder, $v_1$: a volume ratio of the gas or liquid, $v_2$: a volume ratio of the powder, k: fitting parameter ($-1 \leq k \leq 1$), and u: fitting parameter ($0 \leq u$)

By using these Equations, the dielectric constant $\in_2$ of the powder is calculated. For example, in the case in which the dielectric constant $\in_2$ of the powder is to be calculated from the dielectric constant $\in$ of the mixture obtained by mixing the powder and the air by using the air as the gas, the dielectric constant $\in_1$ of the air in these Equations is known as "1.0". Moreover, the volume ratio $v_1$ of the air and the volume ratio $v_2$ of the powder are determined by an amount of the powder to be put in the space of the waveguide, respectively. If the dielectric constant $\in$ of the mixture obtained by mixing the powder and the air is apparent, accordingly, the dielectric constant $\in_2$ of the powder can be obtained.

EXAMPLES

In order to cause the advantages of the invention to be clearer, examples will be given below.

Example 1

There were prepared a sample A of powder-like $Al_2O_3$ having a density of 3.99 g/cm$^3$ and a mean particle size of 9.8 μm, a sample B of powder-like $Al_2O_3$ having a density of 3.99 g/cm$^3$ and a mean particle size of 17.8 μm, and a sample C of powder-like $Al_2O_3$ having a density of 3.99 g/cm$^3$ and a mean particle size of 134.7 μm.

By using, as a measuring device, the measuring device 12 shown in FIG. 2, the sample A was filled in the closed space formed in a cavity resonator 14 in order to have a volume ratio of 0.39, and the dielectric constant and the dielectric loss tangent of a layer 118 of a mixture obtained by mixing the sample A and the air in a vacuum were measured.

First of all, a second piston 140 was inserted from below a through hole 116 having a diameter of 16 mm which is formed on the cavity resonator 14, and was positioned and fixed with a screw 134b. Furthermore, a first piston 120 was inserted from above the through hole 116 and was positioned in such a manner that a thickness $L_1$ of an air layer 112 was 12 mm, and the first piston 120 was fixed with a screw 134a and the air resonator 14 was filled with the air.

Next, an electromagnetic wave having a frequency of GHz or more was output from a network analyzer 16 into the cavity resonator 14 through a coaxial cable 122 and a loop antenna 124.

Moreover, the electromagnetic wave output from the cavity resonator 14 was received by the loop antenna 124 and was input to the network analyzer 16 through the coaxial cable 122 in response to the input of the electromagnetic wave.

Subsequently, a resonance frequency $f_1$ in a $TE_{011}$ mode of a resonance mode, an insertion loss $IL_1$ and a half-power width $\Delta f_1$ at the resonance frequency $f_1$, and a resonance frequency $f_2$ in a $TE_{012}$ mode were measured from the input electromagnetic wave through the coaxial cable 122.

Thus, the resonance frequency $f_1$ in the $TE_{011}$ mode, the insertion loss $IL_1$ and the half-power width $\Delta f_1$ at the resonance frequency $f_1$, and the resonance frequency $f_2$ in the $TE_{012}$ mode which were measured by the network analyzer 16 were output from the network analyzer 16 to a calculating device 18.

The resonance frequency $f_1$ in the $TE_{011}$ mode, the insertion loss $IL_1$ and the half-power width $\Delta f_1$ at the resonance frequency $f_1$, and the resonance frequency $f_2$ in the $TE_{012}$ mode were output from the network analyzer 16 to the calculating device 18, and thereafter, the first piston 120 was once removed from the through hole 116 and 3.13 g of the sample A was put into the through hole 116. By using a piston having a flat tip portion of a cylinder constituting the piston, differently from the first piston 120, pressurization was subsequently carried out in such a manner that a thickness $L_2$ of the layer 118 of the mixture obtained by mixing the sample A and the gas was 10 mm, and the surface of the sample A was made smooth and the first piston 120 was inserted from above the through hole 116 again, and the position of the first piston 120 was adjusted in such a manner that the thickness L1 of the air layer 112 was 2 mm and the first piston 120 was thus fixed with the screw 134a.

Furthermore, the electromagnetic wave was output from the network analyzer 16 through the coaxial cable 122 and the loop antenna 124 to the cavity resonator 14 filled with the sample A, and the electromagnetic wave output from the cavity resonator 14 was received by the loop antenna 124 in response to the input of the electromagnetic wave and was input to the network analyzer 16 through the coaxial cable 122.

A resonance frequency $f_3$ in the $TE_{011}$ mode of the resonance mode, and an insertion loss $IL_3$ and a half-power width $f_3$ at the resonance frequency $f_3$ were measured by the network analyzer 16 from the input electromagnetic wave through the coaxial cable 122.

Thus, the resonance frequency $f_3$ in the $TE_{011}$ mode, and the insertion loss $IL_3$ and the half-power width $f_3$ at the resonance frequency $f_3$ which were measured by the network analyzer 16 were output from the network analyzer 16 to the calculating device 18.

By the calculating device 18, next, the resonance frequency $f_1$, the insertion loss $IL_1$, the half-power width $\Delta f_1$ and the resonance frequency $f_2$ which were input from the network analyzer 16 were substituted for the Equations (1) to (3) to calculate an effective conductivity σ of the internal wall of the cavity resonator 14, $Q_1$ to be an unload Q value of the cavity resonator 14 in a state in which the closed space of the cavity resonator 14 was not filled with the sample A, and an apparent diameter D of the closed space of the cavity resonator 14.

By the calculating device 18, furthermore, the resonance frequency $f_3$, the half-power width $\Delta f_3$, and the insertion loss $IL_3$, the apparent diameter D of the closed space of the cavity resonator 14 which had already been obtained, the thickness $L_1$ of the layer 112 of the air filled in the closed space, and the thickness $L_2$ of the layer 118 of the mixture obtained by mixing the sample A, and the air were substituted for the Equations (4) and (5) to calculate Q3 to be an unload Q value of the cavity resonator 14 in a state in which the cavity resonator 14 was filled with the sample A, and a dielectric constant $\in_{r2}$ of the layer 118 of the mixture obtained by mixing the sample A and the air.

By the calculating device 18, subsequently, the effective conductivity σ which had already been calculated, $Q_3$ to be the unload Q value of the cavity resonator 14 in the state in which the cavity resonator 14 was filled with the sample A, the apparent diameter D of the closed space, the thickness $L_1$ of the layer 112 of the gas filled in the closed space, and the thickness $L_2$ Of the layer 118 of the mixture obtained by mixing the sample A and the gas were substituted for the Equation (6) to calculate the dielectric loss tangent of the layer 118 of the mixture obtained by mixing the sample A and the gas.

Thus, there were obtained the dielectric constant $\in_{r2}$ and the dielectric loss tangent of the layer 118 of the mixture having a volume ratio of 0.39 and obtained by mixing the sample A and the air.

Next, the mass of the sample A to be filled in the closed space formed in the cavity resonator 14 was changed to gradually vary the volume ratio of the sample A up to 0.54, thereby calculating the dielectric constant $\in_{r2}$ and the dielectric loss tangent of the layer 118 of the mixture obtained by mixing the sample A and the air in the same manner as in the case in which the sample A has a volume ratio of 0.39.

By the calculating device 18, furthermore, a dielectric constant $\in_r$ of the sample A was obtained from the dielectric constant $\in_{r2}$ of the layer 118 of the mixture obtained by mixing the sample A and the air at a different volume ratio in the following manner.

In order to enhance precision in the measurement of the dielectric constant $\in_r$ of the sample A, first of all, the dielectric constant $\in_{r2}$ of the layer 118 of the mixture obtained by mixing the sample A and the air and having various volume ratios was fitted to the logarithmic alligation, the equation of "Lichteneker Rother" and the equation of Wiener by the least square method in consideration of the measuring error of the dielectric constant $\in_{r2}$ of the layer 118 of the mixture obtained by mixing the sample A and the air and having various volume ratios. Thus, there was created a graph in which an axis of abscissa indicates the volume ratio of the sample A and an axis of ordinate indicates the dielectric constant $\in_{r2}$ of the layer 118 of the mixture obtained by mixing the sample A and the air.

Figure 11:
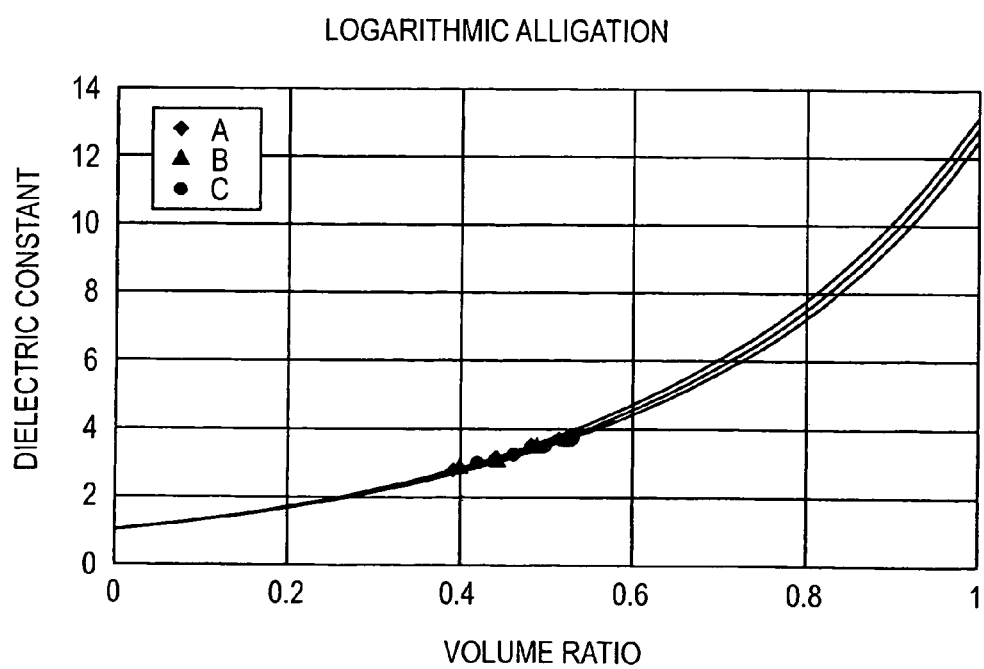
FIG. 11 is a graph obtained by fitting dielectric constants $\in_{r2}$ of mixtures having various volume ratios in which a sample A and air are mixed with each other to a logarithmic alligation by the least square method.
Figure 12:
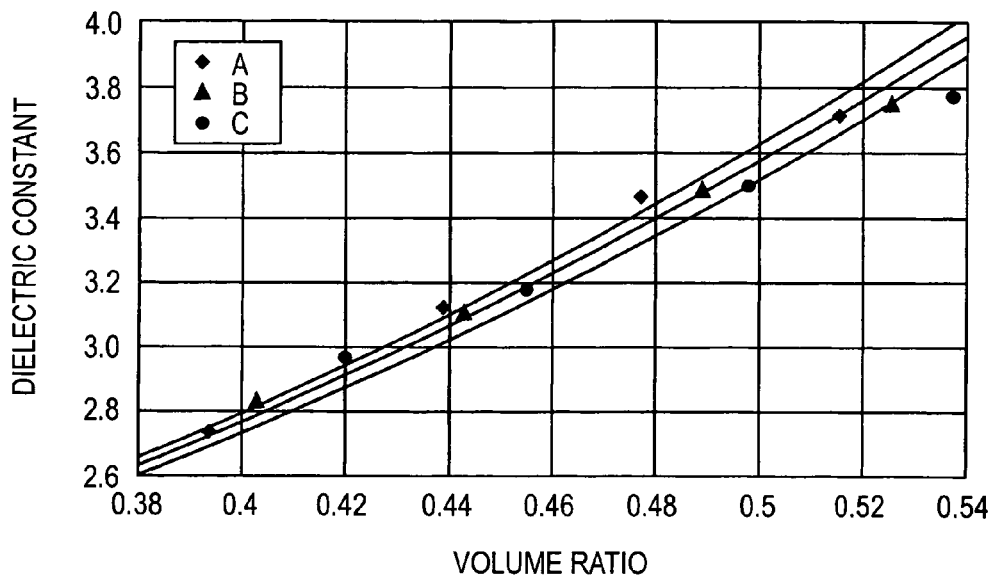
FIG. 12 is a partially enlarged chart of FIG. 11.

FIGS. 11 and 12 are graphs obtained by fitting the dielectric constant $\in_{r2}$ of the layer 118 of the mixture obtained by mixing the sample A and the air and having various volume ratios to the logarithmic alligation by the least square method, and FIG. 12 is a graph obtained by enlarging the graph of FIG. 11, in which the volume ratio of the sample A ranges from 0.38 to 0.54.

Figure 13:
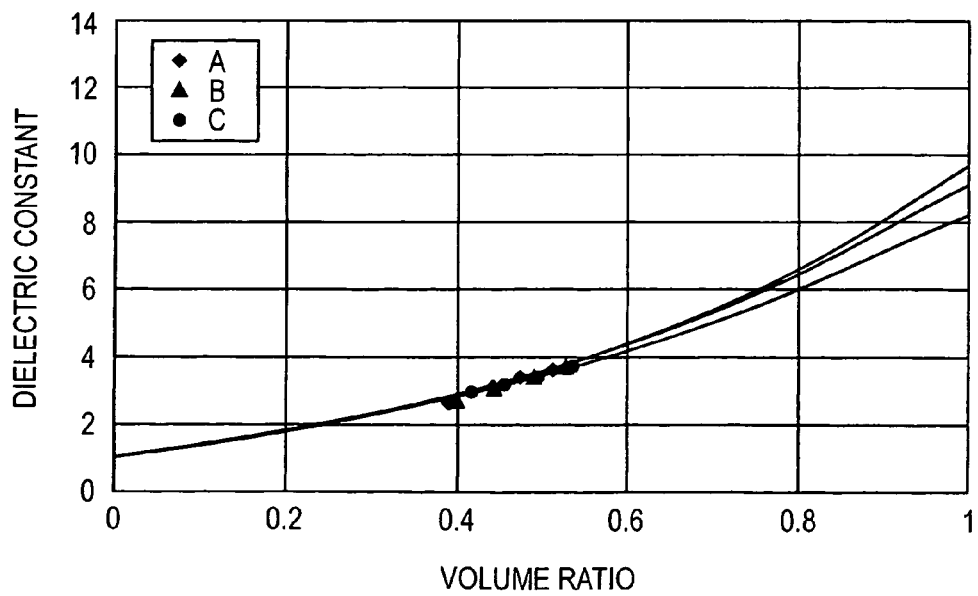
FIG. 13 is a graph obtained by fitting the dielectric constants $\in_{r2}$ of the mixtures having various volume ratios in which the sample A and the air are mixed with each other to an equation of "Lichtneker Rother" by the least square method.
Figure 14:
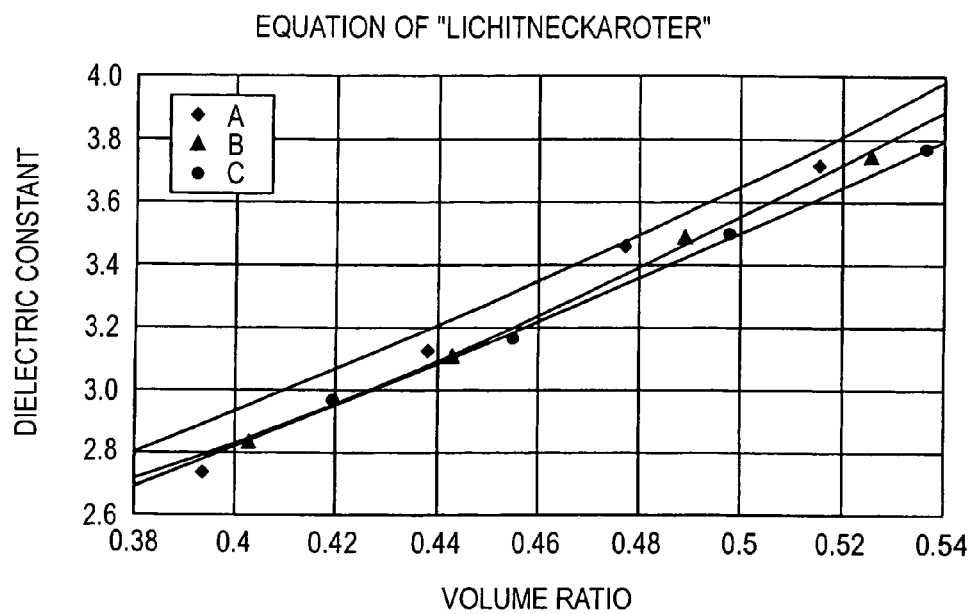
FIG. 14 is a partially enlarged chart of FIG. 13.

FIGS. 13 and 14 are graphs obtained by fitting the dielectric constant $\in_{r2}$ of the layer 118 of the mixture obtained by mixing the sample A and the air and having various volume ratios to the equation of "Lichteneker Rother" by the least square method, and FIG. 14 is a graph obtained by enlarging the graph of FIG. 13, in which the volume ratio of the sample A ranges from 0.38 to 0.54.

Figure 15:
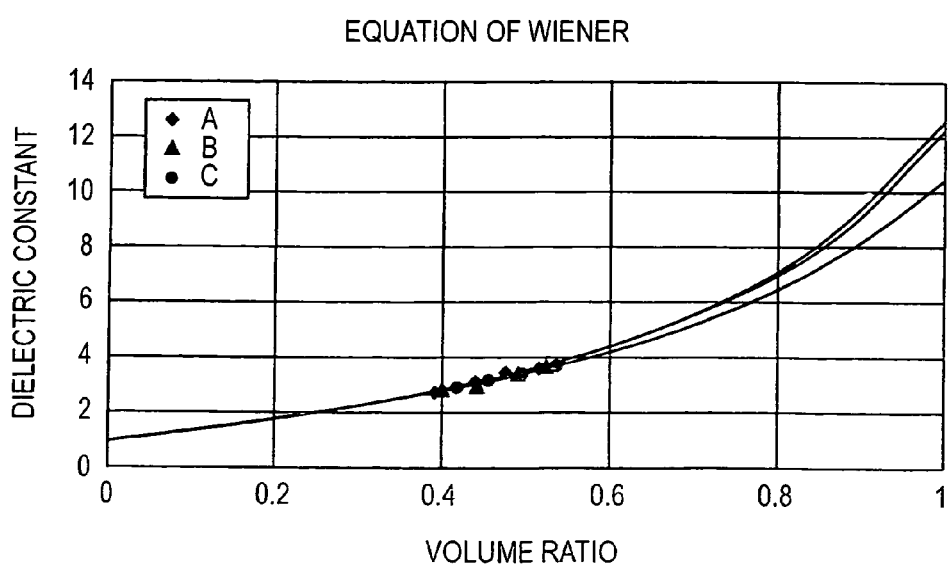
FIG. 15 is a graph obtained by fitting the dielectric constants $\in_{r2}$ of the mixtures having various volume ratios in which the sample A and the air are mixed with each other to an equation of Wiener by the least square method.
Figure 16:
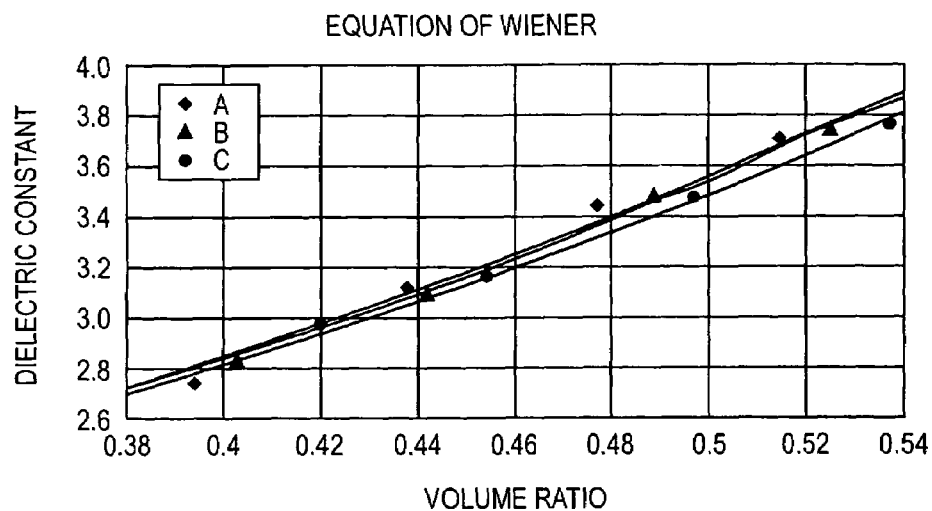
FIG. 16 is a partially enlarged chart of FIG. 15.

FIGS. 15 and 16 are graphs obtained by fitting the dielectric constant $\in_{r2}$ of the layer 118 of the mixture obtained by mixing the sample A and the air and having various volume ratios to the equation of Wiener by the least square method, and FIG. 16 is a graph obtained by enlarging the graph of FIG. 15, in which the volume ratio of the sample A ranges from 0.38 to 0.54.

In FIGS. 11, 13 and 15, 1.0 of the volume ratio of the sample A implies that the air is not present in the layer 118 of the mixture obtained by mixing the sample A and the air but only the sample A is present in the layer 118 of the mixture obtained by mixing the sample A and the air. For this reason, the value of the dielectric constant with 1.0 of the volume ratio of the sample A corresponds to the dielectric constant $\in_r$ Of the sample A. Accordingly, the value of the dielectric constant with 1.0 of the volume ratio of the sample A was read from curves shown in FIGS. 11, 13 and 15, thereby obtaining the dielectric constant $\in_r$ of the sample A.

Thus, the dielectric constant $\in_r$ of the sample A was obtained.

By the calculating device 18, furthermore, the dielectric loss tangent of the sample A was obtained from the dielectric loss tangent of the layer 118 of the mixture obtained by mixing the sample A and the air at various volume ratios in the following manner.

In order to enhance precision in the measurement of the dielectric loss tangent of the sample A, the dielectric loss tangent of the layer 118 of the mixture obtained by mixing the sample A and the air and having various volume ratios was substituted for the equation of an alligation in consideration of the measuring error of the dielectric loss tangent of the layer 118 of the mixture obtained by mixing the sample A and the air and having various volume ratios, and a relationship between the volume ratio of the sample A and the dielectric loss tangent of the layer 118 of the mixture obtained by mixing the sample A and the air was approximated by a straight line passing through an origin. Thus, a graph shown in FIG. 17 was created.

Figure 17:
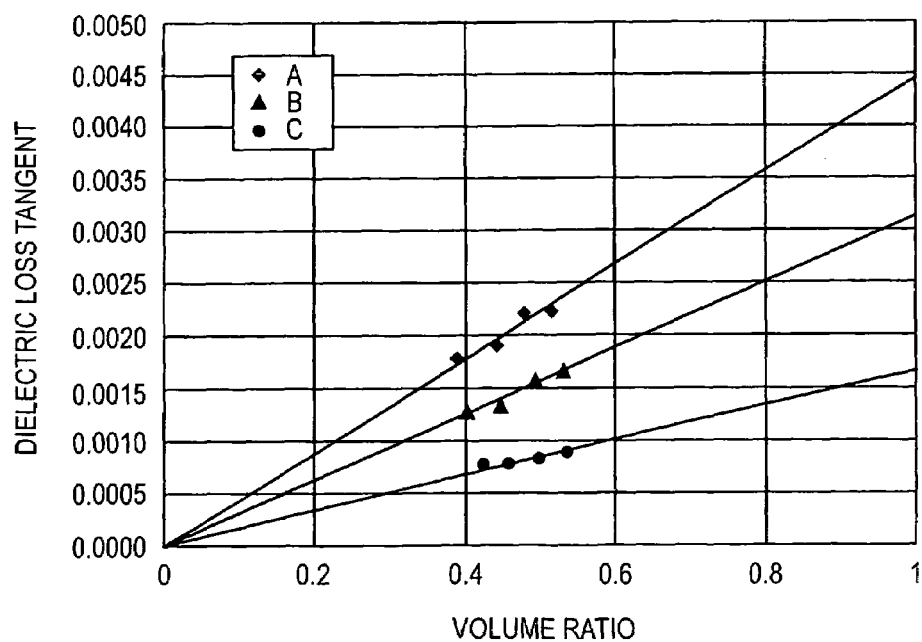
FIG. 17 is a graph obtained by substituting, for an alligation, the dielectric loss tangents of the mixtures having various volume ratios in which the sample A and the air are mixed with each other, and approximating a relationship between the volume ratio of the sample A and the dielectric loss tangent of the mixture obtained by mixing the sample A and the air through a straight line passing through an origin.
Figure 18:
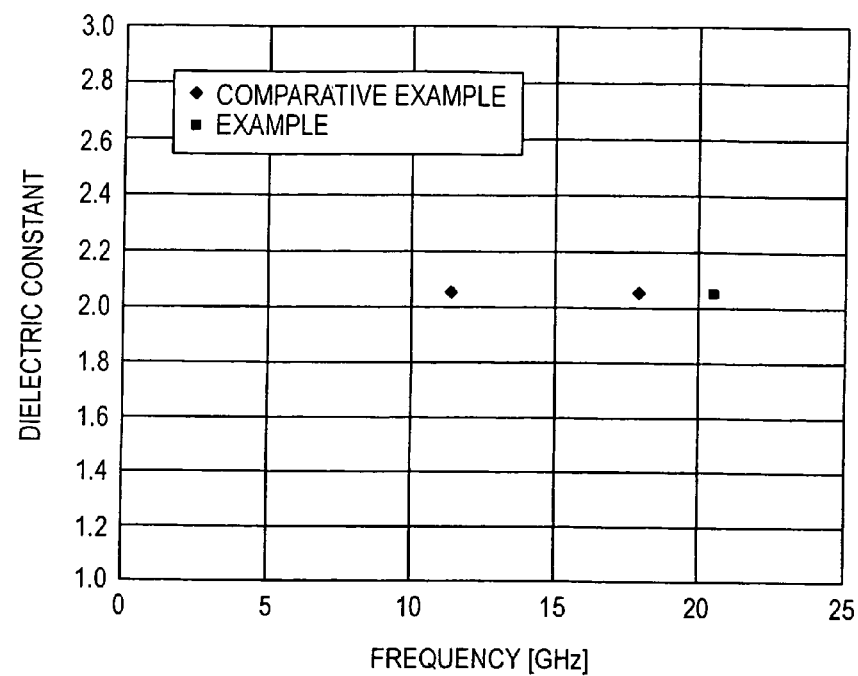
FIG. 18 is a graph showing a result obtained by measuring the dielectric constant of a tetrafluoroethylene cylinder and that of a sheet-like tetrafluoroethylene.
Figure 19:
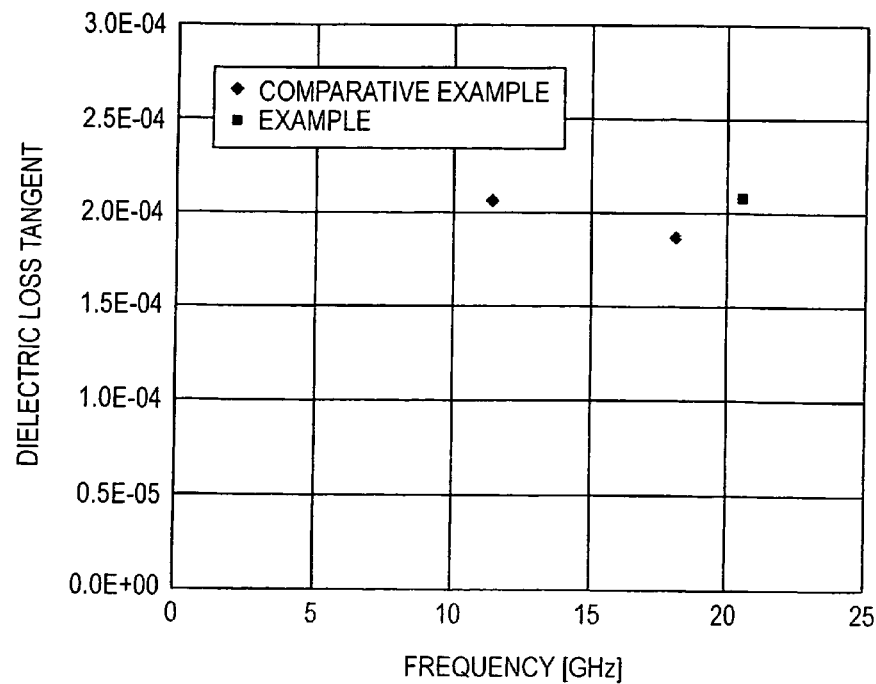
FIG. 19 is a graph showing a result obtained by measuring the dielectric loss tangent of the tetrafluoroethylene cylinder and that of the sheet-like tetrafluoroethylene.

In FIG. 17, 1.0 of the volume ratio of the sample A implies that the air is not present in the layer 118 of the mixture obtained by mixing the sample A and the air but only the sample A is present in the layer 118 of the mixture obtained by mixing the sample A and the air. For this reason, the value of the dielectric loss tangent with 1.0 of the volume ratio of the sample A corresponds to the dielectric loss tangent of the sample A. Accordingly, the value of the dielectric constant with 1.0 of the volume ratio of the sample A was read from straight lines shown in FIG. 17, thereby obtaining the dielectric loss tangent of the sample A.

In the same manner as in the case in which the dielectric constant $\in_r$ and the dielectric loss tangent of the sample A were measured, subsequently, the dielectric constant $\in_r$ and the dielectric loss tangent of the sample B were obtained.

More specifically, in the same manner as in the case in which the dielectric constant $\in_r$ and the dielectric loss tangent of the sample A were measured, the mass of the sample B to be filled in the closed space formed in the cavity resonator 14 was changed to vary the volume ratio of the sample B within a range of 0.39 to 0.54. Thus, the dielectric constant $\in_{r2}$ and the dielectric loss tangent of the layer 118 of the mixture obtained by mixing the sample B and the air were obtained and the dielectric constant $\in_r$ and the dielectric loss tangent of the sample B were obtained.

In the same manner as in the case in which the dielectric constants $\in_r$ and the dielectric loss tangents of the samples A and B were measured, furthermore, the dielectric constant $\in_r$ and the dielectric loss tangent of the sample C were obtained.

The results of the measurement for the dielectric constants $\in_r$ and the dielectric loss tangents of the samples A, B and C are shown in Table 1.

TABLE 1

| Symbol | Logarithmic alligation | Equation of "Lichteneker Rother" | Equation of Wiener | Dielectric loss tangent |
|---|---|---|---|---|
| A | 13.11 | 9.14 | 12.34 | 0.0044 |
| B | 12.72 | 9.63 | 12.77 | 0.0031 |
| C | 12.33 | 8.27 | 10.58 | 0.0017 |

As shown in the Table 1, values ranging from 8.3 to 13.1 were obtained as the dielectric constants of the samples A, B and C. According to the invention, it was found that the dielectric constant of a powder-like dielectric at a frequency in order of GHz or more can be measured.

According to the invention, moreover, it was also apparent that the dielectric loss tangent of the powder-like dielectric at a frequency of GHz or more can be measured.

Example 2

A tetrafluoroethylene cylinder having a thickness of 8.05 mm and a diameter of 16 mm was prepared for the measuring object of a dielectric constant and a dielectric loss tangent, and a thickness $L_1$ of an air layer obtained before filling the cavity resonator 14 with the tetrafluoroethylene cylinder was set to be 10.05 mm. In the same manner as in the Example 1, the dielectric constant and the dielectric loss tangent of the tetrafluoroethylene cylinder were measured.

More specifically, the cavity resonator 14 was filled with the tetrafluoroethylene cylinder and a gas, and an electromagnetic wave was input from the network analyzer 16 into the cavity resonator 14, and a resonance frequency $f_3$, a half-power width $\Delta f_3$ and an insertion loss $IL_3$ in a TE mode of the electromagnetic wave input to the network analyzer 16 from the cavity resonator 14 to which the electromagnetic wave was input were measured to obtain a dielectric constant $\in_{r2}$ and a dielectric loss tangent of the tetrafluoroethylene cylinder.

Comparative Example

As a comparative example with the Example 2, a sheet-like tetrafluoroethylene having a thickness of 1.04 mm was prepared. By using a cavity resonator method defined in JIS standards, the dielectric constant and the dielectric loss tangent of the sheet-like tetrafluoroethylene at a frequency of 11.4 GHz and 17.9 GHz were obtained.

In the Example 2 and the comparative example, Table 2 shows a result obtained by the measurement of the dielectric constant and the dielectric loss tangent of the tetrafluoroethylene cylinder and those of the sheet-like tetrafluoroethylene.

TABLE 2

| | Frequency [GHz] | Dielectric constant | Dielectric loss tangent |
|---|---|---|---|
| Example 1 | 20.6 | 2.05 | 0.00021 |
| Comparative example | 11.4 | 2.06 | 0.00021 |
| Comparative example | 18.0 | 2.06 | 0.00019 |

In the Example 2 and the comparative example, moreover, Table 18 shows a result obtained by measuring the dielectric constant of the tetrafluoroethylene cylinder and that of the sheet-like tetrafluoroethylene.

In the Example 2 and the comparative example, moreover, Table 19 shows a result obtained by measuring the dielectric loss tangent of the tetrafluoroethylene cylinder and that of the sheet-like tetrafluoroethylene.

The dielectric constant of the tetrafluoroethylene cylinder according to the Example 2 and that of the sheet-like tetrafluoroethylene according to the comparative example have almost equal values to each other, that is, approximately 2.05.

Furthermore, the dielectric loss tangent of the cylindrical tetrafluoroethylene according to the Example 2 and that of the sheet-like tetrafluoroethylene according the comparative example had almost equal values to each other, that is, approximately 0.0002.

Example 3

In Example 3, the waveguide 210 shown in FIG. 8 was applied as the wave guiding device 201. In the Example, moreover, air was used as a gas. Accordingly, the mixture 213 of FIG. 8 contains a powder to be measured and the air. In the Example, furthermore, the thickness of the mixture 213 was approximately 20 mm in such a state as to be filled in the waveguide 210.

As a sample to be measured by using the waveguide 210, in the embodiment, powders of three kinds of ceramics materials ($Al_2O_3$ ceramics, $Ba(MgTa)O_3$ ceramics and $TiO_2$ ceramics) were prepared. The mixture 213 containing each powder and the air was prepared and the dielectric constant of the mixture 213 containing each powder and the air was measured by using the dielectric characteristic measuring device 200. In order to make a comparison with a result obtained by measuring the dielectric constant of the mixture by using a waveguide 220 according to Example 4 which will be described below, moreover, the dielectric constant was also measured for $Ba (Nd, Bi)_2Ti_5O_{14}$ ceramics. The result of the comparison will be described in the explanation of the Example 4. In the Example 3, an electromagnetic wave having a frequency of 5 GHz was incident on each mixture 213 and the dielectric constant was measured in response thereto. The volume ratio of the powder in the mixture 213 was changed between 0.32 and 0.42 to measure the dielectric constant of each mixture 213.

Figure 20:
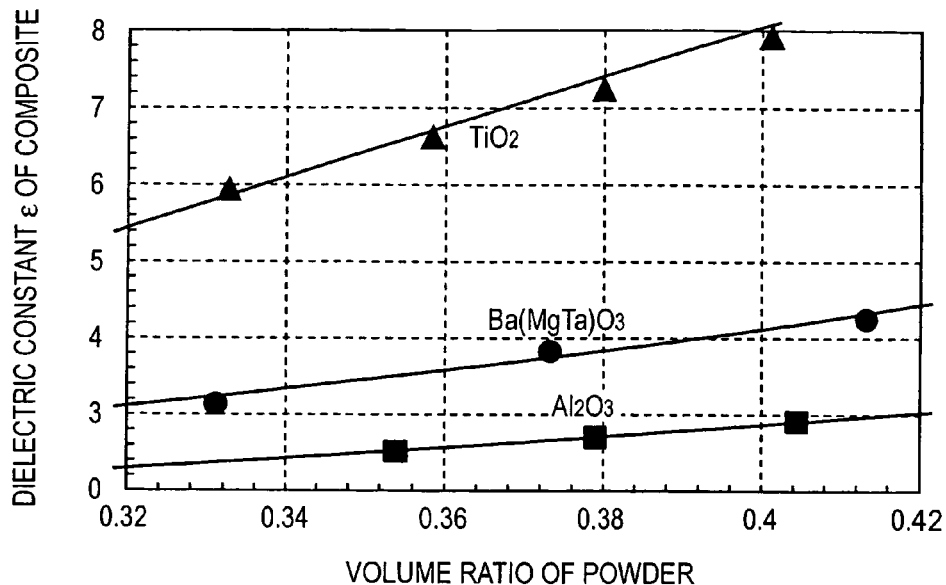
FIG. 20 is a graph showing a measured value of the dielectric constant of a composite and a result obtained by applying the logarithmic alligation to the measured value.
Figure 21:
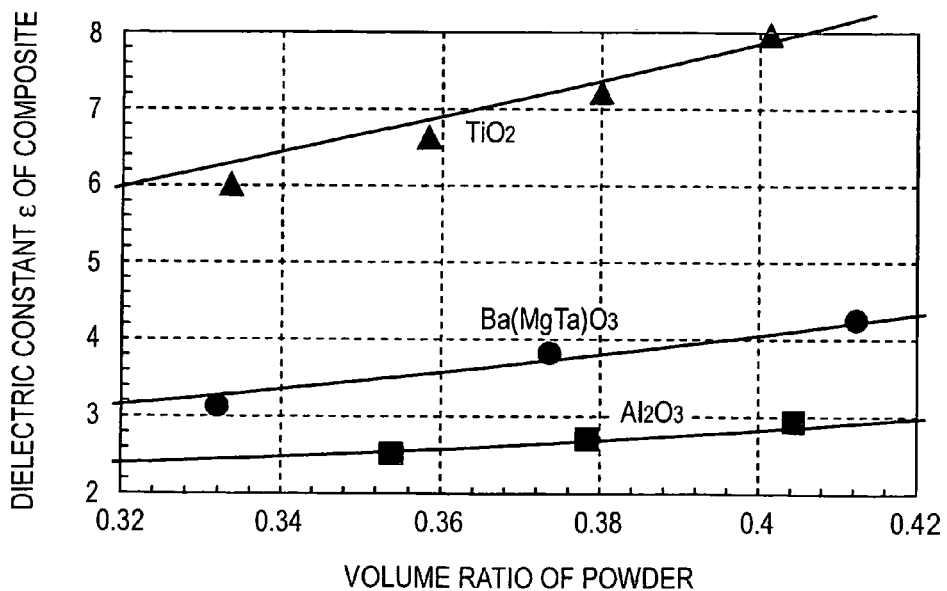
FIG. 21 is a graph showing the measured value of the dielectric constant of the composite and a result obtained by applying the equation of "Lichteneker Rother" to the measured value.
Figure 22:
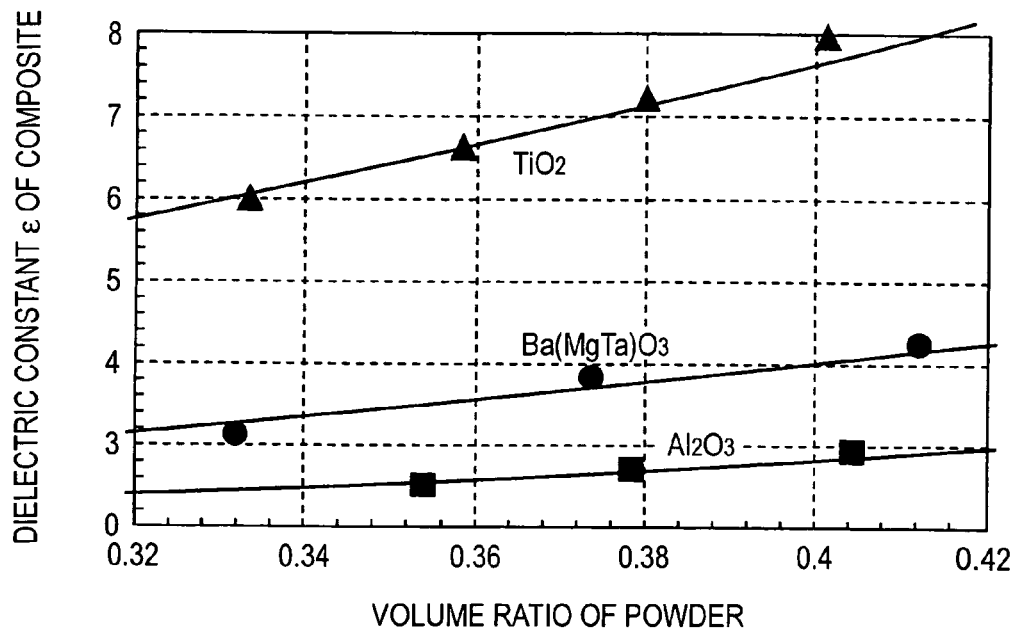
FIG. 22 is a graph showing the measured value of the dielectric constant of the composite and a result obtained by applying the equation of Wiener to the measured value.

A dielectric constant $\in$ of the mixture 213 containing the powder and the air thus obtained is applied to the logarithmic alligation, the equation of "Lichteneker Rother" or the equation of Wiener. FIGS. 20 to 22 show a measured value of the dielectric constant of each mixture 213 which is obtained by using the waveguide 210 according to the Example 3 and a result obtained by applying an equation to the measured value. Curves shown in these drawings are obtained by fitting each measured value of the dielectric constant of the mixture 213 into each equation by the least square method. FIG. 20 is a chart showing a measured value of the dielectric constant of each mixture 213 and a result obtained by applying the logarithmic alligation to the measured value. FIG. 21 is a chart showing a measured value of the dielectric constant of each mixture 213 and a result obtained by applying the equation of "Lichtneker Rother" to the measured value. FIG. 22 is a chart showing a measured value of the dielectric constant of each mixture 213 and a result obtained by applying the equation of Wiener to the measured value.

Figure 23:
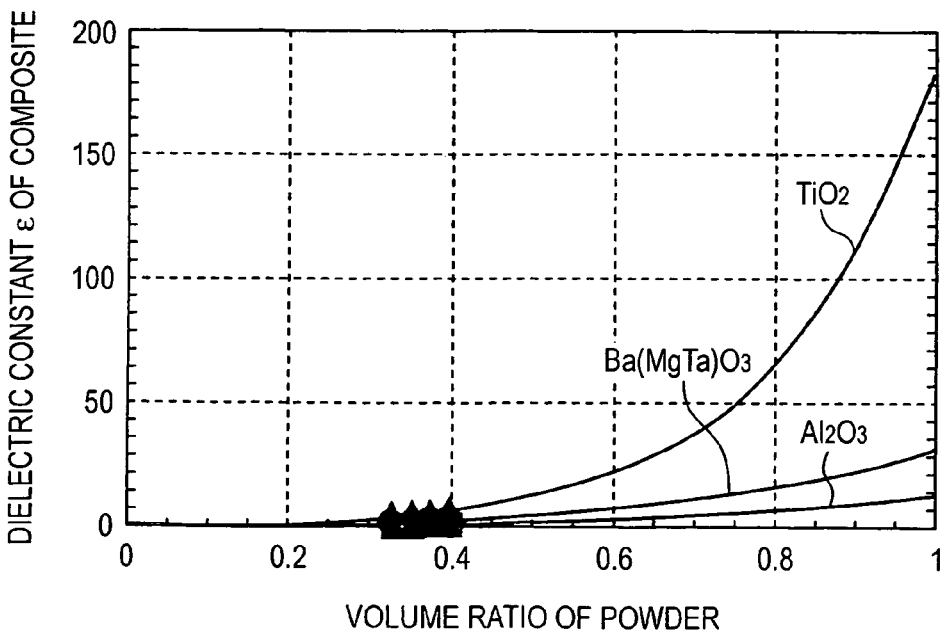
FIG. 23 is a graph to be used for applying the logarithmic alligation to calculate the dielectric constant of a powder.
Figure 24:
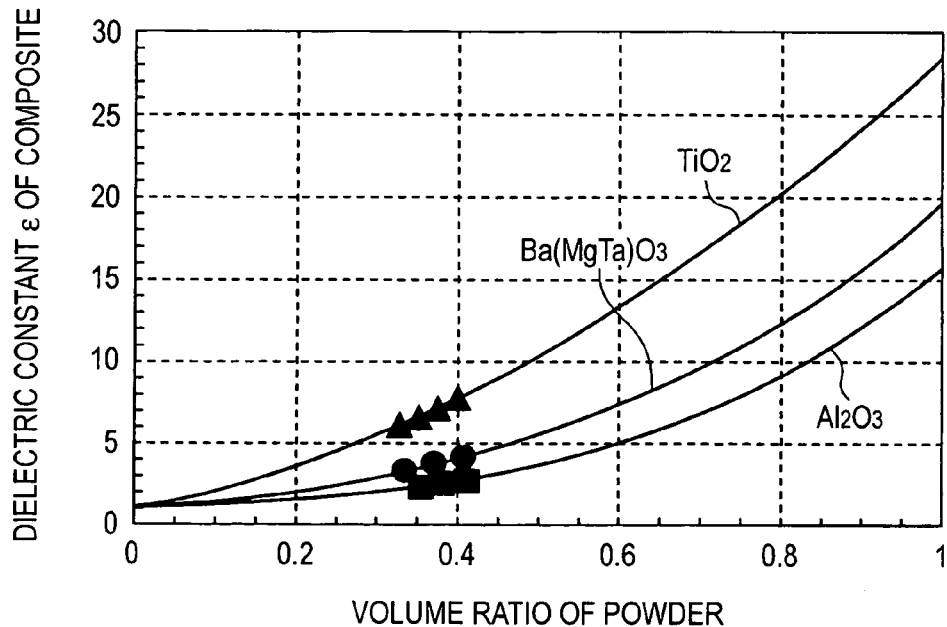
FIG. 24 is a graph to be used for applying the equation of "Lichteneker Rother" to calculate the dielectric constant of the powder.
Figure 25:
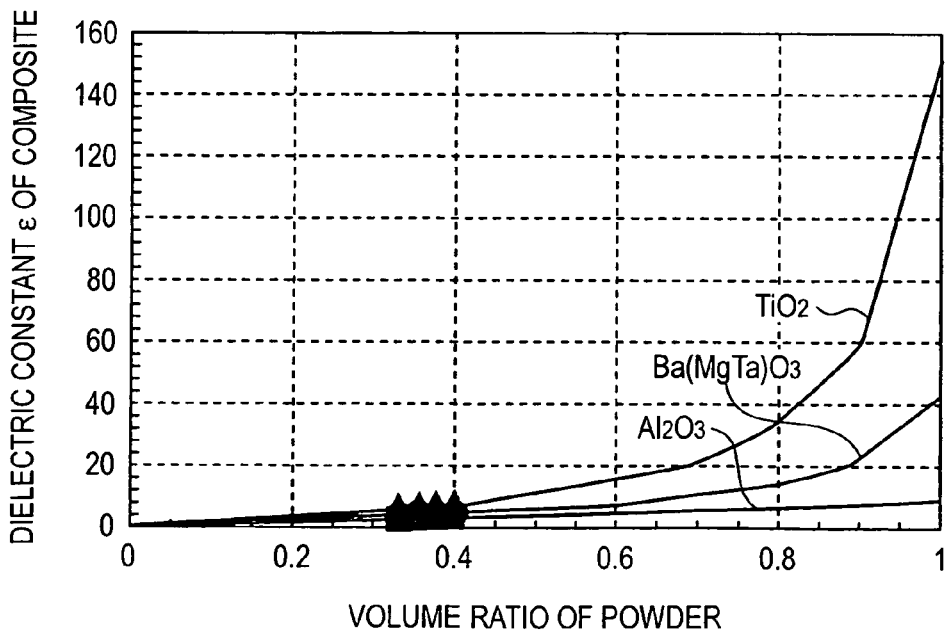
FIG. 25 is a graph to be used for applying the equation of Wiener to calculate the dielectric constant of the powder.

By using the results of the measurement, it is possible to analogize the dielectric constant of the powder itself. FIGS. 23 to 25 show graphs for analogizing the dielectric constant of the powder. In order to analogize the dielectric constant of the powder, an equation such as the logarithmic alligation is used to fit each measured value of the dielectric constant of the mixture 213 into each equation by the least square method, thereby calculating a curve for analogizing the dielectric constant of the powder. By calculating the dielectric constant $\in$ of the mixture containing the air and the powder when the volume ratio of the powder is "1.0", it is possible to disregard the presence of the air in the mixture containing the air and the powder, thereby analogizing a dielectric constant $\in_2$ of the powder itself.

FIG. 23 is a chart showing a result obtained by fitting the measured value of the dielectric constant of each mixture 213 to the logarithmic alligation by the least square method. FIG. 24 is a chart showing a result obtained by fitting the measured value of the dielectric constant of each mixture 213 to the equation of "Lichteneker Rother" by the least square method. FIG. 25 is a chart showing a result obtained by fitting the measured value of the dielectric constant of each mixture 213 to the equation of Wiener by the least square method. In these drawings, it is possible to analogize the dielectric constant of the powder itself by reading the value of the dielectric constant with "1.0" of the volume ratio of the powder. The dielectric constant of each powder obtained from FIGS. 23 to 25 is collectively shown in FIGS. 26 to 28.

FIGS. 26 to 28 are tables in which the dielectric constant of each powder obtained by applying each of the equations shown in FIGS. 23 to 25 is compared with the dielectric constant of a sintered product. FIG. 26 is a table showing the dielectric constant of each powder obtained by applying the logarithmic alligation to a measured value. FIG. 27 is a table showing the dielectric constant of each powder obtained by applying the equation of "Lichteneker Rother" to a measured value. FIG. 28 is a table showing the dielectric constant of each powder obtained by applying the equation of Wiener to a measured value.

As a result of the application of the logarithmic alligation as shown in FIG. 26, the dielectric constant of the sintered product of $Al_2O_3$ ceramics was "11", while a result obtained by the measuring method according to the invention was "14.1". Moreover, the dielectric constant of the sintered product of $Ba(MgTa)O_3$ ceramics was "24", while a result obtained by the measuring method according to the invention was "33.9". Furthermore, the dielectric constant of the sintered product of $TiO_2$ ceramics was "104", while a result obtained by the measuring method according to the invention was "185.8".

As a result of the application of the equation of "Lichteneker Rother" as shown in FIG. 27, moreover, the dielectric constant of the sintered product of the $Al_2O_3$ ceramics was "11", while the result obtained by the measuring method according to the invention was "15.7". Moreover, the dielectric constant of the sintered product of the $Ba (MgTa)O_3$ ceramics was "24", while the result obtained by the measuring method according to the invention was "19.4". Furthermore, the dielectric constant of the sintered product of the $TiO_2$ ceramics was "104", while the result obtained by the measuring method according to the invention was "28.2".

As a result of the application of the equation of Wiener as shown in FIG. 28, furthermore, the dielectric constant of the sintered product of the Al$_2$O$_3$ ceramics was "11", while the result obtained by the measuring method according to the invention was "8.75". Moreover, the dielectric constant of the sintered product of the Ba (MgTa)O$_3$ ceramics was "24", while the result obtained by the measuring method according to the invention was "42.7". Furthermore, the dielectric constant of the sintered product of the TiO$_2$ ceramics was "104", while the result obtained by the measuring method according to the invention was "152.3".

From the above results, in the Example 3, it was possible to measure the dielectric constant of the mixture containing the powder and the air at a frequency of 5 GHz by using the waveguide 210. From the results, furthermore, it was possible to guess the dielectric constant of the powder itself.

Figures 29, 30:
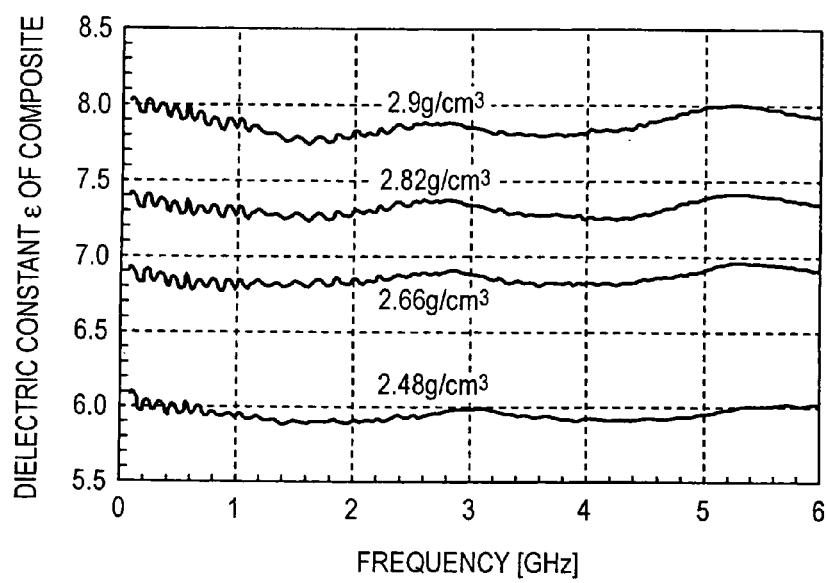
FIG. 29 is a chart showing a result obtained by measuring the frequency dependency of the dielectric constant of a mixture by using a waveguide.
FIG. 30 is a table obtained by relatively comparing the dielectric constants of powders made of different materials.

Next, FIG. 29 shows a result obtained by checking the frequency dependency of the dielectric constant of the mixture 213. As a sample, Ba(Nd, Bi)$_2$Ti$_5$O$_{14}$ was used to measure the dielectric constant of the mixture 213 for an individual density which is obtained when the density of the powder in the mixture 213 containing the powder and the air was changed. Then, a frequency region was changed from 0.1 GHz to 6 GHz to measure the dielectric constant $\in$ of the mixture 213. As shown in FIG. 29, it was apparent that the dielectric constant of the mixture 213 does not depend on a frequency in the frequency region of 0.1 GHz to 6 GHz. By using the waveguide 210 in the Example 3, accordingly, the same results as those in the case of the execution of the measurement at 5 GHz could be obtained between 0.1 GHz and 6 GHz at a frequency other than 5 GHz.

With reference to FIGS. 20 and 30, next, the dielectric constants of the powders formed by different materials are relatively compared with each other. First of all, there is read a dielectric constant on a point where the volume ratio of the powder in the mixture 213 is "0.38" in FIG. 20, for example.

FIG. 30 shows the read value. As a result, the read value of the Al$_2$O$_3$ ceramics was "2.7", the read value of the Ba(MgTa)O$_3$ ceramics was "3.8", and the read value of the TiO$_2$ ceramics was "7.3". The dielectric constant has a relationship in an ascending order of the Al$_2$O$_3$ ceramics, the Ba(MgTa)O$_3$ ceramics and the TiO$_2$ ceramics. On the other hand, the dielectric constant of the sintered product also has a relationship in an ascending order of the Al$_2$O$_3$ ceramics, the Ba (MgTa)O$_3$ ceramics and the TiO$_2$ ceramics.

Accordingly, the relationship of the dielectric constant of each powder obtained by the above method is coincident with that of the dielectric constant of the sintered product. Therefore, the relative comparison of the relationship of the dielectric constants of the powders formed by different materials can be carried out by the above method.

While the relative comparison is carried out by using the result obtained by applying the logarithmic alligation in the Example 3, it is not restricted in the invention. Even if the relative comparison is carried out by using the result obtained by applying the equation of "Lichteneker Rother" or the equation of Wiener, the same result can be obtained. While the volume ratio of the powder is set to be "0.38", moreover, this value is not restricted but the same result can be obtained even if another volume ratio is used to carry out the comparison.

Example 4

In Example 4, the waveguide 220 shown in FIG. 9 was applied as the wave guiding device 201. Also in the Example 4, air was used as a gas. Accordingly, the mixture 223 contains a powder to be measured and the air.

Also in the Example 4, in the same manner as in the Example 3, the mixture 223 containing each powder and the air was prepared by using a powder made of three kinds of ceramics materials (Al$_2$O$_3$ ceramics, Ba(MgTa)O$_3$ ceramics and TiO$_2$ ceramics). By using the dielectric characteristic measuring device 200, the dielectric constant of the mixture 223 containing each powder and the air was measured. In order to make a comparison with the result of the measurement of the waveguide 210 in the Example 3, moreover, the dielectric constant of Ba (Nd, Bi)$_2$Ti$_5$O$_{14}$ ceramics was measured. In the Example 4, an electromagnetic wave having a frequency of 20 GHz was incident on each mixture 223 to measure the dielectric constant in response thereto. In the same manner as in the Example 3, then, the volume ratio of the powder in the mixture 223 was changed to measure the dielectric constant of each mixture 223.

Figure 31:
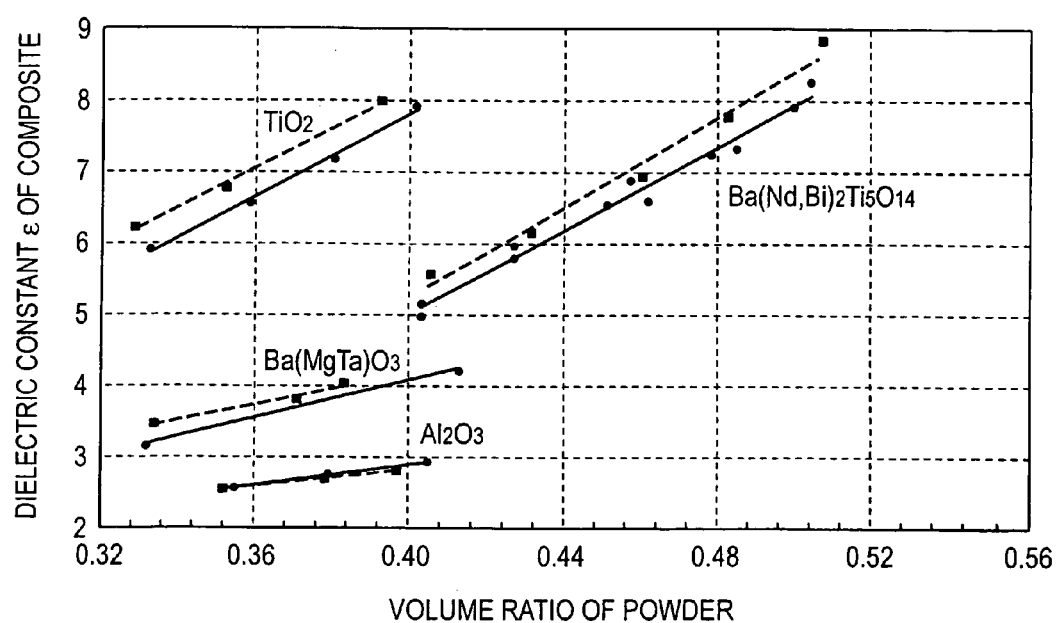
FIG. 31 is a graph showing a comparison with the dielectric constant of the powder obtained by utilizing two kinds of waveguides.

A dielectric constant $\in$ of the mixture 223 containing the powder and the air thus obtained is applied to the logarithmic alligation, the equation of "Lichteneker Rother" or the equation of Wiener. The dielectric constant obtained in the Example 4 was compared with the dielectric constant obtained in the Example 3. The result of the comparison is shown in FIG. 31. FIG. 31 is a graph representing a comparison of the dielectric constant of the mixture 223 obtained by using the waveguide 220 in the Example 4 with that of the mixture 213 obtained by using the waveguide 210 in the Example 3.

In FIG. 31, a broken line represents the dielectric constant of the mixture 223 measured by the waveguide 220 used in the Example 4. On the other hand, a solid line represents the dielectric constant of the mixture 213 measured by the waveguide 210 used in the Example 3. As shown in FIG. 31, it is apparent that the dielectric constant of each mixture measured by using the waveguide 220 is almost coincident with the dielectric constant of each mixture measured by using the waveguide 210. By using the waveguide 220 according to the Example 4, accordingly, it is possible to further measure the dielectric constant of a powder also in a high frequency region as compared with the waveguide 210. In the same manner as in the Example 3, moreover, the dielectric constants of different powders can be relatively compared with each other also in the Example 4.

By using the waveguide 230, in the same manner as in the Examples 3 and 4, the dielectric constant $\in$ of the mixture 233 is measured and the logarithmic alligation, the equation of "Lichteneker Rother" or the equation of Wiener is applied to the measured value so that the dielectric constant of each powder can be analogized. By using the dielectric constant of the mixture obtained by the waveguide 230, in the same manner as in the Example 3, it is possible to compare the dielectric constants of the different powders with each other.

The invention is not restricted to the structure described above but various changes can be made within the scope of the invention described in the Claims. It is apparent that they are included in the scope of the invention.

For example, in the structure, the $TE_{011}$ mode is used as the resonance mode in which a resonance frequency, an insertion loss and a half-power width are to be measured. It is not always necessary to use the $TE_{011}$ mode as the resonance mode in which the resonance frequency, the insertion loss and the half-power width are to be measured, and it is also possible to use a TE mode or a TM mode in addition to the $TE_{011}$.

While the cavity resonator is used as the resonator in the structure, moreover, it is not always necessary to use the cavity resonator as the resonator but it is also possible to use a coaxial resonator and a dielectric resonator.

While the cavity resonator is formed cylindrically in the structure, furthermore, it is not always necessary to form the cavity resonator cylindrically.

While the air is used as the gas to be mixed with the dielectric in the structure, moreover, it is not always necessary to mix the air but it is also possible to mix an argon gas or a nitrogen gas with the dielectric.

While the closed space in the cavity resonator is filled with the air in the structure, furthermore, it is not always necessary to fill the closed space of the cavity resonator with the air. In place of the air, the closed space in the cavity resonator may be filled with a dielectric having a low loss.

While the closed space in the cavity resonator is filled with the air in the structure shown in FIG. 2, moreover, it is not always necessary to fill the closed space in the cavity resonator with the air but it is also possible to fill the closed space in the cavity resonator with the dielectric to evacuate the inside of the closed space in the cavity resonator.

While the screws 134a and 134b are used to fix the first cylinder 28 and the first cylinder 44 in the structure, furthermore, it is not always necessary to use the screws 134a and 134b in order to fix the first cylinder 28 and the second cylinder 44. It is also possible to insert a plate between the cylinder and the first disk 26, thereby fixing the first cylinder 28 or to insert a plate between the cylinder and the second disk 42, thereby fixing the second cylinder 44.

Moreover, the annular groove 32 is formed on the tip portion of the first cylinder 28 in the structure. If a resonance frequency in the $TE_{011}$ mode and a resonance frequency in the $TM_{111}$ mode can be separated from each other, the shape of the tip portion of the first cylinder 28 is not particularly restricted but an annular conductor plate or dielectric plate may be attached to the tip portion of the first cylinder 28 and the groove 32 does not always need to be formed on the tip portion of the first cylinder 28.

Furthermore, the annular groove 32 is formed on the tip portion of the first cylinder 28 in the structure. If a resonance frequency in the $TE_{011}$ mode and a resonance frequency in the $TM_{111}$ mode can be separated from each other, the annular groove 32 does not always need to be formed on the tip portion of the first cylinder 28 but may be formed on the tip portion of the second cylinder 44. Moreover, an annular conductor plate or dielectric plate may be attached to the tip portion of the second cylinder 44.

While the loop antenna 124 is attached to the tip portion of the coaxial cable 122 inserted in the two through holes 30a and 30b formed on the first disk 26 and the first cylinder 28 in the structure, moreover, the two loop antennas 124 do not always need to be attached to the first disk 26 and first cylinder 28 side. More specifically, two through holes may be formed on the second disk 42 and the second cylinder 44 and the loop antenna 124 may be attached to the tip portion of the coaxial cable 122 inserted in the through holes thus formed. Moreover, one through hole may be formed on the first disk 26 and first cylinder 28 and the second disk 42 and second cylinder 44, and the loop antenna 124 may be attached to the tip portion of the coaxial cable 122 inserted in the through hole thus formed.

What is claimed is:

1. A method of measuring a complex dielectric constant of a dielectric, comprising the steps of:
    filling a mode generator with the dielectric, the filling of the mode generator comprising
        disposing first and second pistons opposite one another to form a gap therebetween, and disposing a cylinder to contact portions of exterior walls of each of the first and second pistons and to form a closed space to receive the dielectric;
    inputting an electromagnetic wave to the mode generator;
    measuring an electromagnetic wave output from the mode generator; and
    calculating the complex dielectric constant based on the measured electromagnetic wave.

2. The method of measuring a complex dielectric constant of a dielectric according to claim 1, wherein the dielectric is a powder-like dielectric,
    the mode generator is filled with a gas together with the dielectric,
    an S parameter of the electromagnetic wave is measured at the measuring step, and
    the calculating step includes a step of calculating a complex dielectric constant of a mixture obtained by mixing the dielectric and the gas in the mode generator based on the S parameter, and
    a step of calculating the complex dielectric constant of the dielectric from the complex dielectric constant of the mixture which is calculated and a volume ratio of the dielectric in the mixture.

3. The method of measuring a complex dielectric constant of a dielectric according to claim 2, wherein the calculation of the complex dielectric constant of the mixture is a calculation of a dielectric constant of the mixture, and the calculation of the complex dielectric constant of the dielectric is a calculation of a dielectric constant of the dielectric.

4. The method of measuring a complex dielectric constant of a dielectric according to claim 3, wherein the dielectric constant of the dielectric is calculated by using one of a logarithmic alligation, an equation of "Lichteneker Rother" and an equation of Wiener.

5. The method of measuring a complex dielectric constant of a dielectric according to any of claims 2 to 4, wherein the calculation of the complex dielectric constant of the mixture is a calculation of a dielectric loss tangent of the mixture, and the calculation of the complex dielectric constant of the dielectric is a calculation of a dielectric loss tangent of the dielectric.

6. The method of measuring a complex dielectric constant of a dielectric according to claim 5, wherein the calculation of the dielectric loss tangent of the dielectric is carried out by using an equation of the alligation.

7. The method of measuring a complex dielectric constant of a dielectric according to claim 1, wherein the dielectric is a dielectric molding having the same section as a section of a closed space of the mode generator, the mode generator is filled with a gas together with the dielectric, a resonance frequency, an insertion loss and a half-power width in a resonance mode of the electromagnetic wave are measured at the measuring step, and a complex dielectric constant of the dielectric molding is calculated, at the calculating step, from the resonance frequency, the insertion loss and the half-power width which are thus measured.

8. The method of measuring a complex dielectric constant of a dielectric according to claim 7, wherein the calculation of the complex dielectric constant of the dielectric molding is a calculation of a dielectric constant of the dielectric molding.

9. The method of measuring a complex dielectric constant of a dielectric according to claim 7, wherein the calculation of the complex dielectric constant of the dielectric molding is a calculation of a dielectric loss tangent of the dielectric molding.

10. The method of measuring a complex dielectric constant of a dielectric according to claim 7, wherein the dielectric molding is columnar.

11. The method of measuring a complex dielectric constant of a dielectric according to claim 2 or 7, wherein the mode generator is a cylindrical resonator.

12. The method of measuring a complex dielectric constant of a dielectric according to claim 2 or 7, wherein the mode generator is a cavity resonator.

13. The method of measuring a complex dielectric constant of a dielectric according to claim 2 or 7, wherein the resonance mode of the electromagnetic wave is a TE011 mode.

14. The method of measuring a complex dielectric constant of a dielectric according to claims 1, 2, or 7, further comprising a step of drying the dielectric in the mode generator.

15. The method of measuring a complex dielectric constant of a dielectric according to claim 14, further comprising a step of evacuating the mode generator, thereby drying the dielectric.

16. The method of measuring a complex dielectric constant of a dielectric according to claim 1, wherein the mode generator is a waveguide, the waveguide is filled with a gas or a liquid together with the dielectric, a dielectric constant of a mixture obtained by mixing a powder and the gas or liquid is calculated based on the measured electromagnetic wave at the calculating step, and a dielectric constant of the powder is calculated from the dielectric constant of the mixture and a volume ratio of the powder in the mixture at the calculating step.

17. The method of measuring a complex dielectric constant of a dielectric according to claim 16, wherein a dielectric constant of the dielectric is calculated by using one of a logarithmic alligation, an equation of "Lichteneker Rother" and an equation of Wiener.

18. The method of measuring a complex dielectric constant of a dielectric according to claim 16, wherein the waveguide is a coaxial-type waveguide.

19. The method of measuring a complex dielectric constant of a dielectric according to claim 16, wherein the waveguide is a rectangular waveguide.

20. The method of measuring a complex dielectric constant of a dielectric according to claim 16, wherein the waveguide is a circular waveguide.

21. The method of measuring a complex dielectric constant of a dielectric according to claim 16, wherein the waveguide includes a seal portion for holding the gas or the liquid.

22. The method of measuring a complex dielectric constant of a dielectric according to claim 16, wherein a volume ratio of the powder in the mixture is set to be 0.32 to 0.42 and a frequency of the electromagnetic wave is 0.1 GHz or more.

23. The method of measuring a complex dielectric constant of a dielectric according to claim 17, further comprising the steps of:

measuring respective dielectric constants of a plurality of mixtures in which types of powders are different from each other and volume ratios are equal to each other, and comparing the dielectric constants of the mixtures, thereby comparing and measuring dielectric constants of a plurality of dielectrics.

24. An apparatus for measuring a complex dielectric constant of a dielectric, comprising:

a mode generator having the dielectric provided therein, the mode generator comprising a resonator including top and bottom pistons and a cylinder, the top and bottom pistons disposed opposite one another to form a gap therebetween, and the cylinder disposed to contact portions of exterior walls of each of the top and bottom pistons and to form a closed space to receive the dielectric;

an electromagnetic wave generating analyzer for inputting an electromagnetic wave to the mode generator provided with the dielectric and measuring the electromagnetic wave output from the mode generator in response to the input of the electromagnetic wave; and a calculating device for calculating the complex dielectric constant of the dielectric based on the measured electromagnetic wave.

25. The apparatus for measuring a complex dielectric constant of a dielectric according to claim 24, wherein the resonator is configured to receive a gas therein, the electromagnetic wave generating analyzer measures a resonance frequency, an insertion loss and a half-power width in a resonance mode of the electromagnetic wave, and the calculating device calculates the complex dielectric constant of the dielectric based on the resonance frequency, the insertion loss and the half-power width.

26. The apparatus for measuring a complex dielectric constant of a dielectric according to claim 25, wherein the first piston is provided with a through hole and the resonator comprises a coaxial cable for inputting and outputting the electromagnetic wave, the cable being inserted in the through hole.

27. The apparatus for measuring a complex dielectric constant of a dielectric according to claim 26, wherein an annular groove is formed on a tip portion of the first piston and a tip portion of the second piston.

28. The apparatus for measuring a complex dielectric constant of a dielectric according to claim 26, wherein an annular conductor plate or dielectric plate is attached to a tip portion of the first piston and a tip portion of the second piston.

29. The apparatus for measuring a complex dielectric constant of a dielectric according to claim 25, wherein when the dielectric is a powder, the calculating device calculates a complex dielectric constant of a mixture obtained by mixing the dielectric and the gas in the resonator from the resonance frequency, the insertion loss and the half-power width which are measured, and calculates the complex dielectric constant of the dielectric from the complex dielectric constant of the mixture which is thus calculated and a volume ratio of the dielectric in the mixture.

30. The apparatus for measuring a complex dielectric constant of a dielectric according to claim 29, wherein the calculation of the complex dielectric constant of the mixture is a calculation of a dielectric constant of the mixture, and the calculation of the complex dielectric constant of the dielectric is a calculation of a dielectric constant of the dielectric.

31. The apparatus for measuring a complex dielectric constant of a dielectric according to claim 30, wherein the dielectric constant of the dielectric is calculated by using one of a logarithmic alligation, an equation of "Lichteneker Rother" and an equation of Wiener.

32. The apparatus for measuring a complex dielectric constant of a dielectric according to claim 29, wherein the calculation of the complex dielectric constant of the mixture is a calculation of a dielectric loss tangent of the mixture, and the calculation of the complex dielectric constant of the dielectric is a calculation of a dielectric loss tangent of the dielectric.

33. The apparatus for measuring a complex dielectric constant of a dielectric according to claim 32, wherein the dielectric loss tangent of the dielectric is calculated by using an equation of the alligation.

34. The apparatus for measuring a complex dielectric constant of a dielectric according to claim 25, wherein when the columnar dielectric is a molding, the calculating device calculates a complex dielectric constant of the dielectric molding from the resonance frequency, the insertion loss and the half-power width which are measured.

35. The apparatus for measuring a complex dielectric constant of a dielectric according to claim 34, wherein the calculation of the complex dielectric constant of the dielectric molding is a calculation of a dielectric constant of the dielectric molding.

36. The apparatus for measuring a complex dielectric constant of a dielectric according to claim 34, wherein the calculation of the complex dielectric constant of the dielectric molding is a calculation of a dielectric loss tangent of the dielectric molding.

37. The apparatus for measuring a complex dielectric constant of a dielectric according to claim 25, wherein the resonance mode of the electromagnetic wave is a TE011 mode.

38. The apparatus for measuring a complex dielectric constant of a dielectric according to claim 25, further comprising a vacuum device for evacuating a closed space in the resonator to dry the dielectric in the resonator.

39. The apparatus for measuring a complex dielectric constant of a dielectric according to claim 34, wherein the resonator is filled with a columnar dielectric molding having the same section as a section of the closed space and a gas.

40. The apparatus for measuring a complex dielectric constant of a dielectric according to claim 25, wherein the dielectric and the gas are filled in a closed space having an almost circular section which is formed in the resonator.

41. The apparatus for measuring a complex dielectric constant of a dielectric according to claim 24, wherein the mode generator is a waveguide filled with a mixture obtained by mixing a powder of which complex dielectric constant is to be measured and a gas or a liquid.

* * * * *